US006682741B1

(12) United States Patent
Ribaudo et al.

(10) Patent No.: US 6,682,741 B1
(45) Date of Patent: Jan. 27, 2004

(54) β₂ MICROGLOBULIN FUSION PROTEINS AND HIGH AFFINITY VARIANTS

(75) Inventors: Randall K. Ribaudo, Silver Spring, MD (US); Michael Shields, Encinitas, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/719,243

(22) PCT Filed: Jun. 3, 1999

(86) PCT No.: PCT/US99/12309

§ 371 (c)(1),
(2), (4) Date: Mar. 19, 2001

(87) PCT Pub. No.: WO99/64597

PCT Pub. Date: Dec. 16, 1999

Related U.S. Application Data

(60) Provisional application No. 60/088,813, filed on Jun. 10, 1998.

(51) Int. Cl.⁷ .......................... A61K 38/16; C07K 14/74; C07K 14/705; C07H 21/04; C12N 5/10; C12N 15/63
(52) U.S. Cl. .............................. 424/192.1; 424/184.1; 424/185.1; 424/93.1; 424/93.2; 424/93.21; 424/93.7; 530/350; 536/23.1; 536/23.4; 435/325; 435/320.1
(58) Field of Search .................... 530/350; 435/325, 435/320.1; 424/184.1, 185.1, 192.1, 93.1, 93.2, 93.21, 93.7; 536/23.1, 23.4

(56) References Cited

U.S. PATENT DOCUMENTS

| | | | |
|---|---|---|---|
| 5,434,131 A | | 7/1995 | Linsley et al. |
| 5,521,288 A | | 5/1996 | Linsley et al. |
| 5,529,921 A | | 6/1996 | Peterson et al. |
| 5,574,205 A | | 11/1996 | Kucherlapati et al. |
| 5,580,756 A | | 12/1996 | Linsley et al. |
| 5,582,831 A | | 12/1996 | Shinitzky |
| 5,698,679 A | | 12/1997 | Nemazee |
| 5,712,149 A | | 1/1998 | Roberts |
| 5,733,550 A | | 3/1998 | Rock |
| 6,183,734 B1 | * | 2/2001 | Chen et al. |
| 6,451,305 B1 | * | 9/2002 | Boussiotis et al. |
| 2002/0123108 A1 | | 9/2002 | Edwards et al. |

FOREIGN PATENT DOCUMENTS

| | | | |
|---|---|---|---|
| EP | 0 733 373 A2 | | 9/1996 |
| WO | WO 91/16924 | | 11/1991 |
| WO | WO 94/24290 | | 10/1994 |
| WO | WO97/24446 | * | 7/1997 |

OTHER PUBLICATIONS

Bjorkman et al., "Structure of the Human Class I Histocompatibility Antigen, HLA–A2," *Nature* 329:506–512 (1987).
Freeman et al., "Murine B7–2, an Alternative CTLA4 Counter–Receptor that Costimulates T Cell Proliferation and Interleukin 2 Production,"*J. Exp. Med.* 178:2185–2192 (1993).
Freeman et al., "Cloning of B7–2: A CTLA–4 Counter–Receptor that Costimulates Human T Cell Proliferation," *Science* 262:909–911 (1993).
Fukazawa et al., "The Effect of Mutant β₂–Microglubulins on the Conformation of HLA–B27 Detected by Antibody and by CTL," *J. Immunol.* 153:3542–3550 (1994).
Gerstmayer et al., "Costimulation of T Cell Proliferation by a Chimeric B7–2 Antibody Fusion Protein Specifically Targeted to Cells Expressing the erbB2 Proto–Oncogene," *J. Immunol.* 1584584–4590 (1997).
Liu, "The Immunologist's Grail: Vaccines that Generate Cellular Immunity," *Proc. Natl. Acad. Sci. USA* 94:10496–10498 (1997).
Mottez et al., "Cells Expressing a Major Histocompatibility Complex Class I Molecule with a Single Covalently Bound Peptide Are Highly Immunogenic," *J. Exp. Med.* 181:493–502 (1995).
Rock et al., "Peptide–Priming of Cytolytic T Cell Immunity in Vivo Using β₂–Microglobulin as an Adjuvant," *J. Immunol.* 150:1244–1252 (1993).
Shields et al., "The Effect of Human β₂–Microglobulin on Major Histocompatibility Complex I Peptide Loading and the Engineering of a High Affinity Variant," *J. Biol. Chem.* 273:28010–28018 (1998).
Shields et al., "Characterization of the Interactions between MHC Class I Subunits: A Systemic Approach for the Engineering of Higher Affinity Variants of β₂–Microglobulin,"*J. Immunol.* 160:2297–2307 (1998).
Uger et al., "Creating CTL Targets with Epitope–Linked β–MicroglobulinConstructs," *J. Immunol.* 160:1599–1605 (1998).

* cited by examiner

Primary Examiner—Phillip Gambel
Assistant Examiner—Jessica H. Roark
(74) Attorney, Agent, or Firm—Klarquist Sparkman, LLP

(57) ABSTRACT

β₂-microglobulin fusion proteins and modified forms of β₂-microglobulin are disclosed. The fusion proteins are shown to incorporate onto the surface of MHC I expressing mammalian cells and to cause an increased cytotoxic T-cell response to antigens presented by such cells. The fusion proteins are useful in methods of tumor therapy. Modified forms of human β₂-microglobulin, particularly a form having a serine to valine transition at amino acid position 55 of the mature protein are shown to have an enhanced affinity for MHC I heavy chain, and are useful both in the disclosed fusion proteins and as a vaccine adjuvant where enhanced cytotoxic T-cell response is desired.

64 Claims, 7 Drawing Sheets

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
|<u>M</u>|<u>S</u>|<u>R</u>|<u>S</u>|<u>V</u>|<u>A</u>|<u>L</u>|<u>A</u>|<u>V</u>|<u>L</u>|<u>A</u>|<u>L</u>|<u>L</u>|<u>S</u>|<u>L</u>|<u>S</u>|<u>G</u>|<u>L</u>|<u>E</u>|<u>A</u>|V|S|V|E|T|Q|A|Y|F|N|30|
|G|T|A|Y|L|P|C|P|F|T|K|A|Q|N|I|S|L|S|E|L|V|V|F|W|Q|D|Q|Q|K|L|60|
|V|L|Y|E|H|Y|L|G|T|E|K|L|D|S|V|N|A|K|Y|L|G|R|T|S|F|D|R|N|N|W|90|
|T|L|R|L|H|N|V|Q|I|K|D|M|G|S|Y|D|C|F|I|Q|K|K|P|P|T|G|S|I|I|L|120|
|Q|Q|T|L|T|E|L|S|V|I|A|N|F|S|E|P|E|I|K|L|A|Q|N|V|T|G|N|S|G|I|150|
|N|L|T|C|T|S|K|Q|G|H|P|K|P|K|K|M|Y|F|L|I|T|N|S|T|N|E|Y|G|D|N|180|
|M|Q|I|S|Q|D|N|V|T|E|L|F|S|I|S|N|S|L|S|L|S|F|P|D|G|V|W|H|M|T|210|
|V|V|C|V|L|E|T|E|S|M|K|I|S|S|K|P|L|N|F|T|Q|E|F|P|S|P|Q|T|Y|W|240|
|*A*|*S*|*T*|*S*|<u>G</u>|<u>G</u>|<u>G</u>|<u>G</u>|<u>S</u>|<u>G</u>|<u>G</u>|<u>G</u>|<u>G</u>|<u>S</u>|<u>G</u>|<u>G</u>|<u>G</u>|<u>A</u>|<u>S</u>|I|Q|R|T|P|K|I|Q|V|Y|S|270|
|R|H|P|A|E|N|G|K|S|N|F|L|N|C|Y|V|S|G|F|H|P|S|D|I|E|V|D|L|L|K|300|
|N|G|E|R|I|E|K|V|E|H|S|D|L|S|F|S|K|D|W|S|F|Y|L|L|Y|Y|T|E|F|T|330|
|P|T|E|K|D|E|Y|A|C|R|V|N|H|V|T|L|S|Q|P|K|I|V|K|W|D|R|D|M| | |358|

β₂ MICROGLOBULIN FUSION PROTEINS AND HIGH AFFINITY VARIANTS

PRIORITY CLAIM

This application is a U.S. national stage application of PCT/US99/12309, filed Jun. 3, 1999, which was published in English under PCT Article 21(2), which in turn claims the benefit of U.S. Provisional Application No. 60/088,813, filed Jun. 10, 1998.

FIELD OF THE INVENTION

This invention relates to compositions based on $\beta_2$ microglobulin, and the use of such compositions in immunological methods pertaining to the targeting of proteins to cell surfaces. The disclosed compositions and methods have particular application to vaccination and tumor therapy.

BACKGROUND OF THE INVENTION

MHC I and Activation of Cytotoxic T-cells

The beta-2 microglobulin ($\beta_2$m) protein is a component of the class I major histocompatibility complex (MHC I). MHC I is formed by the association of $\beta_2$m and an alpha protein (also known as the "heavy" chain), which comprises three domains, a1, a2 and a3. MHC I is found on the surface of most types of nucleated cells, where it presents antigens derived from proteins synthesized in the cytosol to CD8⁺ T-cells. Two signals are required for activation of naive CD8⁺ T-cells. The first signal is provided by the interaction of the T-cell receptor (TCR) with the MHC I-antigen complex on the antigen-presenting cell surface. The second signal is generated by the interaction of a ligand on the antigen-presenting cell (APC) with a second receptor present on the T-cell surface. This second signal is termed co-stimulation, and the APC ligand is often referred to as a co-stimulatory molecule. The best characterized co-stimulatory molecules on APCs are the structurally related glycoproteins B7.1 (CD80) and B7.2 (CD86) which interact with the CD28 receptor on the T-cell surface. Activation of CD8⁺ T-cells by these two signals leads to the proliferation of antigen-specific cytotoxic T-cells, which recognize and destroy cells presenting the signaling antigen. These cytotoxic T-cells play an important role in the immunological defense against intracellular pathogens such as viruses, as well as tumors. A detailed presentation of the immunological basis of the cytotoxic T-cell response can be found in Janeway and Travers (*Immunobiology: the immune system in health and disease,* Current Biology Ltd./Garland Publishing, Inc. New York, 1997).

The failure of an exogenous (non-self) antigen to stimulate a cytotoxic T-cell response can result from a block in the above-described cytotoxic T-cell activation pathway at one of many points (see Ploegh, 1998, *Science* 280:248–53). Failure of the cytotoxic T-cell activation pathway is of great significance in two particular areas of medicine: vaccination and tumor immunology.

Cytotoxic T-cells and Vaccination

Vaccine technology has focused in recent years on subunit vaccines. Sub-unit vaccines comprise isolated pathogen components, such as viral capsid or envelopes, or synthetic peptides that mimic an antigenic determinant of a pathogen-related protein. For example, U.S. Pat. No. 4,974,168 describes leukemia associated immunogens that are peptides based on envelope proteins of a leukemia-associated virus. However, while sub-unit vaccines can stimulate CD4⁺ helper T-cells (which play a key role in humoral immunity), attempts to stimulate CD8⁺ cytotoxic T-cells in vivo with such vaccines have been largely unsuccessful. It has been postulated that the reason for this is the inability of the exogenously administered vaccine peptide to associate with the MHC I molecules on the cell surface (Liu, 1997, *Proc. Natl. Acad Sci. USA* 94:10496–8). In other words, the block in the cytotoxic T-cell activation pathway occurs at the stage where the antigen is loaded into the MHC I molecule.

One proposed solution to this problem is to combine the antigenic peptide with a molecule that is readily taken up into cells (reviewed by Liu, 1997, *Proc. Natl. Acad Sci. USA* 94:10496–8). Thus, this strategy is based on getting the antigen into the cytosol so that it can join the normal pathway by which antigens are processed for presentation by MHC I. In contrast, Rock et al. (*J. Immunol.* 150:1244–52, 1993) adopted a strategy of enhancing the binding of the vaccine peptide to MHC I already present on the cell surface. Rock et al. (*J. Immunol.* 150:1244–52, 1993) report that the administration of exogenous purified $\beta_2$m along with the vaccine peptide produces enhanced loading of the peptide onto MHC I in vivo and thereby stimulates a cytotoxic T-cell response against the peptide. The use of exogenous $\beta_2$m as a vaccine adjuvant is also described in U.S. Pat. No. 5,733,550 (to Rock et al.), which is incorporated herein by reference.

Tumor Cells and Immune System Evasion

Tumor cell immunity is primarily cell-mediated, involving both CD8⁺ cytotoxic T-cells and CD4⁺ helper T-cells. However, despite the fact that tumor cells express tumor-specific proteins that are not recognized as self-antigens by the immune system, they often escape recognition by the immune system. A number of factors may contribute to the ability of tumor cells to evade immune recognition, including the down-regulation of expression of co-stimulatory proteins. TCR stimulation in the absence of co-stimulatory molecules can result in failure to activate the T-cell and the induction of clonal anergy. Thus, down-regulation of co-stimulatory proteins in tumor cells prevents normal activation of T-cells that do bind to tumor antigens on the cell surface, permitting the tumor cell to escape recognition.

Several research groups have attempted to address this issue by removing tumor cells from a patient, providing exogenous co-stimulatory molecules on the surface of the removed tumor cells and then reintroducing the tumor cells to the patient so that immune recognition can occur. For example, European patent application number 96302009.4 describes a method by which tumor cells are removed from a patient, transfected to express both B7 and CD2 (a co-receptor involved in T-cell adhesion and activation) on the tumor cell surface, and then reintroduced to the patient. The reintroduced cells are reported to stimulate a broad immunological response against both the reintroduced transfected tumor cells and the non-transfected tumor cells within the patient's body, resulting in tumor regression.

Adopting an alternative approach to this problem, Gerstmayer et al. (*J. Immunol.* 158:4584–90, 1997) describe a chimeric B7-antibody protein, in which the antibody is specific for the erbB2 proto-oncogene product. This chimeric molecule localizes specifically on the surface of erbB2 expressing tumor cells, and presents the B7 co-stimulatory molecule to cytotoxic T-cells, resulting in enhanced proliferation of cytotoxic T-cells. Gerstmayer et al. (*J. Immunol.* 158:4584–90, 1997) thus propose that fusion proteins comprising an anti-tumor antibody and a co-stimulatory molecule could be useful as tumor immunotherapeutics. However, this approach would require prior knowledge and characterization of tumor-specific antigens expressed on the tumor cells of each individual patient, and the use of an antibody specific for that particular type of tumor cell.

SUMMARY OF THE INVENTION

The present invention employs various forms of beta-2 microglobulin to address the problems associated with failure of the cytotoxic T-cell activation pathway in both vaccination and tumor therapy. The invention also provides compositions and methods based on $\beta_2$m that are broadly applicable to achieve expression of any desired target protein on the surface of any mammalian cell.

In one embodiment, the invention provides fusion proteins comprising a first amino acid sequence and a second amino acid sequence, wherein the second amino acid sequence is a $\beta_2$-microglobulin. In particular applications, the first amino acid sequence may be a co-stimulatory protein, such as B7.1 or B7.2, or another protein having immunological activity, such as a cytokine, an integrin or a cellular adhesion molecule. Examples of such proteins include interleukins (e.g., IL-2, IL-12), granulocyte-macrophage colony-stimulating factor (GM-CSF), lymphocyte function-associated proteins (e.g., LFA-1, LFA-3) and intercellular adhesion molecules (e,g., ICAM-1, ICAM-2). In other embodiments, the first amino acid sequence of the fusion protein may be any protein that is desired to be expressed on the surface of a cell. It is shown that these fusion proteins are an effective way to target a desired protein, such as B7, to the outer membrane of a cell. ("B7" is used generically to refer to either B7.1 or B7.2).

With respect to tumor therapy, it is shown that expressing on the surface of a tumor cell a fusion protein comprising a $\beta_2$m joined to a co-stimulatory protein can significantly increase the immune response of an animal to the tumor cell. In one example, a fusion protein comprising h$\beta_2$m joined to the co-stimulatory protein B7 (and termed B7-$\beta_2$m) is targeted to the surface of tumor cells, such that the tumor cells present the B7-$\beta_2$m fusion protein to T-cells. These cells are then attenuated and introduced into mice. T-cells removed from these mice were shown to be significantly more active against the same type of tumor cells than equivalent cells from mice treated with tumor cells presenting $\beta_2$m only.

The $\beta_2$m fusion proteins provided by the invention have wide application in that they are useful to target any desired protein to the outer membrane of a cell. These fusion proteins may be targeted to the surface of a cell in a number of ways. In one approach, cells that express MHC I are simply incubated with a preparation of the fusion protein, resulting in the incorporation of the fusion protein onto the cell surface. Alternatively, the fusion protein may be introduced into the cell so that it is incorporated into the MHC I pathway. In another approach, a nucleic acid molecule encoding the fusion protein is introduced into a cell by transformation. Expression of this nucleic acid molecule results in the fusion protein being produced within the cell and exported to the cell membrane. Where the fusion protein is to be introduced into the cytosol for export to the outer membrane, or where it will be expressed by a nucleic acid molecule within the cell, it is desirable to include a signal peptide at the N-terminus of the fusion peptide so that the fusion protein is transported to the outer membrane of the cell. The $\beta_2$m signal peptide may be used for this purpose. In all of these approaches, the result is that the $\beta_2$m fusion protein is presented on the surface of the cell.

In one embodiment, the invention includes nucleic acid molecules encoding the disclosed fusion proteins, as well as nucleic acid vectors comprising such nucleic acid molecules. Transgenic cells comprising these nucleic acid molecules are also provided by the invention. Methods of expressing a $\beta_2$m fusion protein on the surface of a cell are provided by the invention. Such methods include contacting a cell with a fusion protein comprising a first amino acid sequence and a second amino acid sequence wherein the second amino acid sequence is a $\beta_2$m. An alternative method provided by the invention comprises transforming the cell with a nucleic acid molecule encoding such a fusion protein.

The invention further provides methods of enhancing the immune response of an animal to an antigen presented on the surface of a cell. Such methods comprise providing a $\beta_2$m fusion protein on the surface of the cell and administering the cell to the animal. In such applications, the fusion protein preferably comprises $\beta_2$m fused to a co-stimulatory protein, such as B7, or another protein having immunological activity. Expressing the $\beta_2$m fusion protein on the surface of the cell may be accomplished by contacting the cell with the fusion protein, or transforming the cell with a nucleic acid molecule encoding the protein. These methods may be applied to the treatment of tumors; in such treatments, the antigen against which an enhanced immune response is desired is a tumor antigen, and the cell bearing the antigen is a tumor cell. The tumor cell may be removed from the body of a mammal having a tumor, or may be derived from an in vitro propagated tumor cell line. The $\beta_2$m fusion protein is introduced to the tumor cell (e.g., by incubation of the tumor cell with the protein, or by transformation of the tumor cell with a nucleic acid encoding the fusion protein), such that the tumor cell presents the fusion protein on its surface. The tumor cell carrying the fusion protein is then administered to a mammal. In certain embodiments, the tumor cell may be attenuated prior to being administered to the mammal; such attenuation may be accomplished using standard means such as radiation, heat or chemical treatment. Once in the body of the mammal, the combination of tumor antigens and the $\beta_2$m-fusion protein on the surface of the tumor cells are recognized by CD8$^+$ T-cells, resulting in T-cell activation, proliferation and thereby an enhanced cytolytic T-cell response against both the introduced tumor cells and other tumor cells in the mammal that express the same tumor antigen.

The present invention also provides modified human $\beta_2$m (h$\beta_2$m) proteins having an enhanced affinity for MHC I. Such proteins are shown to bind to the alpha chain of MHC I with higher affinity than wild-type h$\beta_2$m and to enhance T-cell recognition of APCs bearing the modified h$\beta_2$m. In particular embodiments, the modified h$\beta_2$m proteins have a valine residue at position 55 in place of the serine residue that is found in the mature form of naturally occurring (i.e., wild-type) h$\beta_2$m . Such modified h$\beta_2$m proteins are referred to as h$\beta_2$m S55V.

h$\beta_2$m S55V is useful as a vaccine adjuvant in place of wild-type h$\beta_2$m. Thus, one aspect of the invention is a vaccine preparation comprising at least one antigen and h$\beta_2$m S55V. h$\beta_2$m S55V may also be utilized in place of wild-type h$\beta_2$m in the fusion proteins discussed above. Additionally, $\beta_2$m fusion proteins may also be employed in such vaccine preparations, either using a wild-type $\beta_2$m or, in the case of h$\beta_2$m, h$\beta_2$m S55V.

Sequence Listing

The nucleic and amino acid sequences listed in the Sequence Listing are shown using standard letter abbreviations for nucleotide bases, and three letter code for amino acids. Only one strand of each nucleic acid sequence is shown, but the complementary strand is understood to be included by any reference to the displayed strand.

Seq. I.D. No. 1 shows the amino acid sequence of wild-type (naturally occurring) hβ$_2$m.

Seq. I.D. No. 2 shows the amino acid sequence of the B7-β$_2$m fusion protein (comprising the B7.2 co-stimulatory molecule).

Seq. I.D. No. 3 shows the amino acid sequence of the B7-β$_2$m fusion protein having the β$_2$m signal sequence joined to the N-terminal of the B7 domain.

Seq. I.D. Nos. 4–7 show primers used to construct hβ$_2$m S55V.

Seq. I.D. Nos. 8 and 9 show primers used to amplify the B7.2 protein.

Seq. I.D. No. 10 shows the amino acid sequence of mature hβ$_2$m S55V.

Seq. I.D. Nos. 11 and 12 show the amino acid linker sequences that can be used between the two domains of a fusion protien.

Seq. I.D. Nos. 13 and 14 show amino acid sequences of signal peptides that can be used to direct the expression of a protein in a cell.

Seq. I.D. No. 15 shows the amino acid sequences for a c-myc tag.

Seq. I.D. Nos. 16–20 show the amino acid sequences for peptides used in the HLA stabilization assay.

BRIEF DESCRIPTION OF THE DRAWINGS

FIG. 1 shows the amino acid sequence of naturally occurring (i.e., wild-type) hβ$_2$m (SEQ ID NO:1); the signal peptide is double underlined and the amino acid numbering starts at the isoleucine residue that is the first residue of the mature protein. The serine at position 55 that is changed to valine in S55V is shown in bold.

FIG. 3 shows the sequence of the B7.2-β$_2$m fusion peptide (SEQ ID NO: 2). Residue 1 is a methionine required for expression, residues 2–220 are the extracellular portion of murine B7-2, residues 221–225 (italics) are a sequence created by the insertion of a restriction site into the nucleic acid sequence, residues 226–240 (underlined) are the linker sequence, and residues 241–339 are the mature form of hβ$_2$m.

FIG. 4 shows the sequence of a B7-β$_2$m fusion peptide (SEQ ID NO: 3) having the hβ$_2$m signal sequence (residues 1–20, double underlined). Residues 21–239 are the extracellular portion of murine B7-2, residues 240–244 (italics) are a sequence created by the insertion of a restriction site into the nucleic acid sequence, residues 245–259 (underlined) are the linker sequence, and residues 260–358 are the mature form of hβ$_2$m.

DETAILED DESCRIPTION OF THE INVENTION

Abbreviations and Definitions

Figure 2:
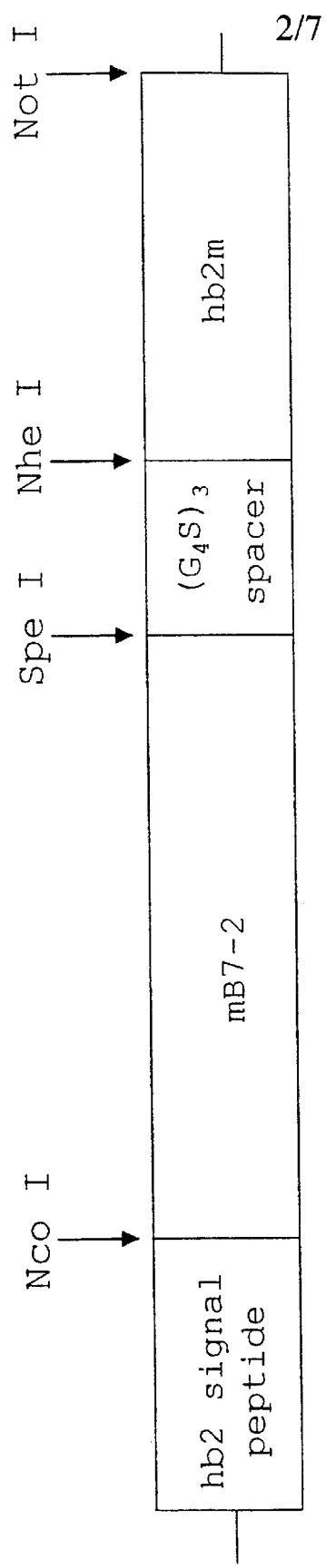
FIG. 2 is a schematic representation of the B7.2-β$_2$ microglobulin fusion peptide construct.

To facilitate review and understanding of the invention as described herein, the following explanation of abbreviations and definitions of terms are provided:

β$_2$m: beta-2 Microglobulin

This term encompasses any mammalian beta-2 microglobulin protein, including human and murine beta-2 microglobulins. The term "hβ$_2$m" refers specifically to human beta-2 microglobulin. cDNAs and genes encoding mammalian β$_2$ms are well known in the art, as are the corresponding β$_2$m protein sequences. Examples include those sequences described in: Parnes and Seidman (*Cell* 29:661–9, 1982), Gates et al. (*Proc. Natl. Acad. Sci. USA* 78:554–8, 1981) (murine); Suggs et al. (*Proc. Natl. Acad. Sci. USA* 78:6613–7, 1981), Guessow et al. (*J. Immunol.* 139:3132–8, 1987), Cunningham et al. (*Biochem.* 12:4811–22, 1973) (human); and Ellis et al. (*Immunogenetics* 38:310, 1993) (bovine). These sequences are also available on the Internet at GenBank's website.

Figures 1, 3:
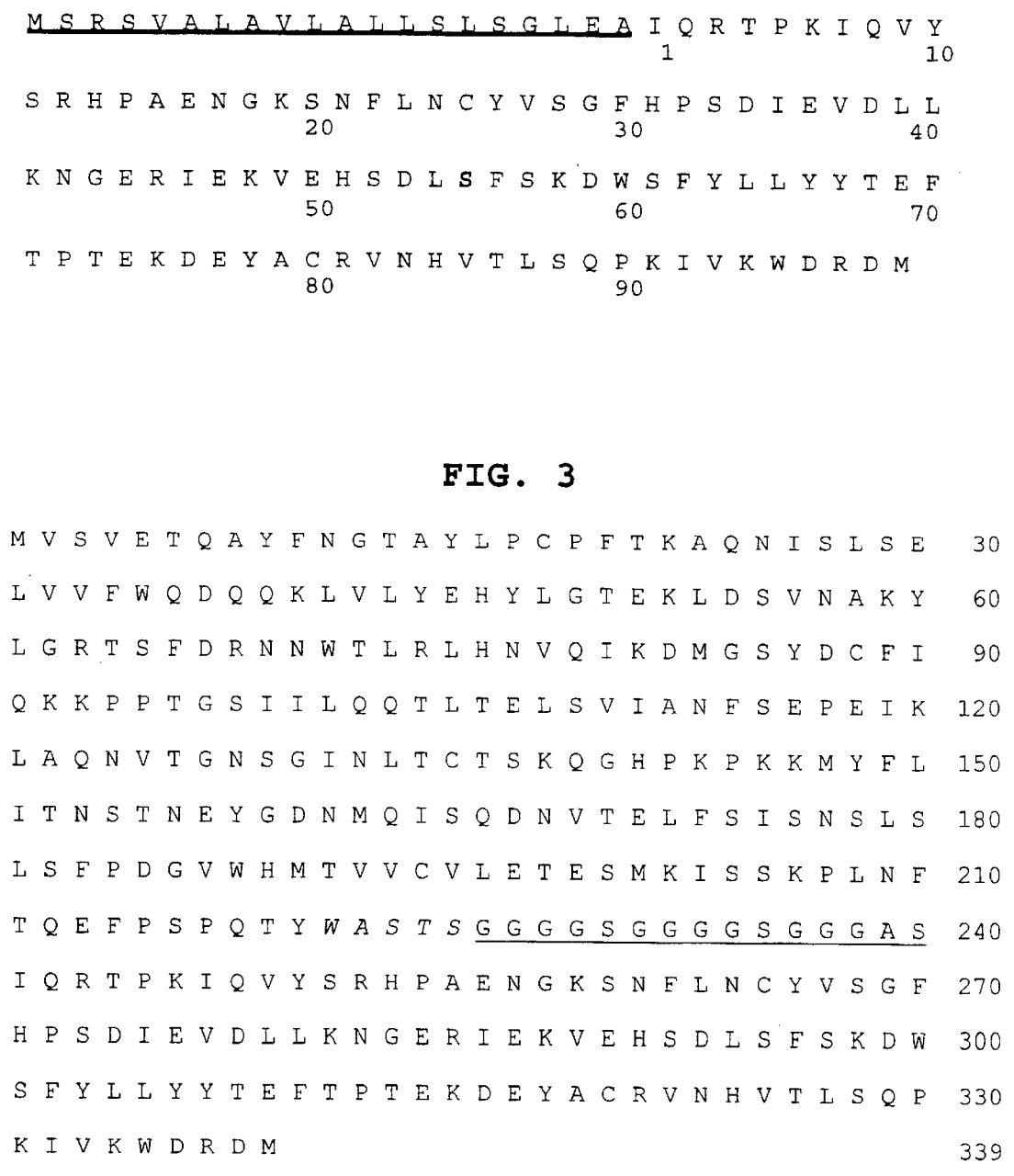

The terms "wild-type β$_2$m" and "naturally occurring β$_2$m" refer to the β$_2$m protein that is isolated from the particular species of mammal in question. For example, wild-type hβ$_2$m refers to a beta-2 microglobulin protein having an amino acid sequence of β$_2$m isolated from a human source (e.g., serum). Thus, an example of a wild-type β$_2$m is the hβ$_2$m protein disclosed in Cunningham et al. (*Biochem.* 12:4811–4822, 1973), which is also available on GenBank under accession number A90371 and is shown in FIG. 1 and Seq. I.D. No. 1. The term "modified β$_2$m" refers to a beta-2 microglobulin protein having an amino acid sequence that has been modified from a wild-type β$_2$m amino acid sequence. By way of example, hβ$_2$m S55V is a mutant form of hβ$_2$m in which the serine residue present at position 55 in mature wild-type hβ$_2$m (see FIG. 1 and Seq. I.D. No. 1) is replaced with a valine residue. The term hβ$_2$m S55V encompasses forms of hβ$_2$m that differ from wild-type hβ$_2$m by the substitution of the position 55 serine for a valine, as well as forms of hβ$_2$m that have the S55V modification and additional amino acid sequence modifications.

Fusion Protein

A protein comprising two amino acid sequences that are not found joined together in nature. The term "β$_2$m fusion protein" refers to a protein that comprises a first amino acid sequence and a second amino acid sequence, wherein the second amino acid sequence is a β$_2$-microglobulin. The β$_2$m amino acid sequence and the first amino acid sequence may alternatively be referred to as domains of the fusion protein. Thus, for example, the present invention provides fusion proteins comprising first and second domains, wherein the second domain is a β$_2$m protein. The link between the first and second domains of the fusion protein is typically, but not necessarily, a peptide linkage. In particular β$_2$m fusion proteins, the two domains may be joined by means of a linker peptide. In β$_2$m fusion proteins, the first domain is preferably, but not necessarily, linked to the N-terminus of the β$_2$m domain.

These fusion proteins may also be represented by the formula X-Y wherein X is a protein, such as a co-stimulatory protein, and Y is a β$_2$m protein. In a further embodiment of the fusion proteins disclosed, a signal peptide sequence may be linked to the N-terminus of the first protein. Such a three part protein can thus be represented as S-X-Y wherein S is the signal peptide, X is a protein, such as a co-stimulatory protein and Y is a $\beta_2$m protein. Where the fusion protein is being expressed in a eukaryotic cell, the signal peptide is preferably a eukaryotic signal peptide that functions to target expression of the fusion protein to the cell membrane. While a number of signal peptides may be used for this purpose, the preferred signal peptide is the $\beta_2$m signal peptide (shown in FIG. 1). Where the fusion protein is being expressed in a prokaryotic cell, the signal peptide is preferably a prokaryotic signal peptide that results in the secretion of the fusion peptide into the growth medium from where it can be readily harvested and purified. Suitable prokaryotic signal peptides are well known in the art. Where the X protein and $\beta_2$m are joined by a peptide linker, the fusion protein may be represented as X-L-Y or, if a signal peptide is present, S-X-L-Y, where L is the linker peptide.

Certain $\beta_2$m fusion proteins of the present invention include, as their $\beta_2$m component, the $h\beta_2$m S55V protein. Particular residues in the $\beta_2$m component of such fusion proteins may be referred to by the number of residues that they are away from the first residue of the mature $h\beta_2$m (which is isoleucine). Thus, the $\beta_2$m component of a fusion protein that includes $h\beta_2$m S55V may be referred to as a human $\beta_2$-microglobulin having a valine at position 55.

Transformed

A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated

An "isolated" biological component (such as a nucleic acid or protein) has been substantially separated or purified away from other biological components in the cell of the organism in which the component naturally occurs, i.e., other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Vector

A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Purified

The term purified does not require absolute purity; rather, it is intended as a relative term. Thus, for example, a purified $\beta_2$m protein preparation is one in which the $\beta_2$m protein is more pure than the protein in its natural environment within a cell. Preferably, a preparation of a protein is purified such that the protein represents at least 50% of the total protein content of the preparation.

Operably linked

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Tumor Cell

A neoplastic cell that may be either malignant or non-malignant. Tumor cells include cells from both solid and non-solid tumors (such as hematologic malignancies). Tumors may be primary tumors originating in a particular organ (such as breast, prostate, bladder or lung). Tumors of the same tissue type may be divided into tumors of different sub-types (a classic example being bronchogenic carcinomas (lung tumors) which can be an adenocarcinoma, small cell, squamous cell, or large cell tumor).

Mammal

This term includes both human and non-human mammals. Similarly, the term "patient" includes both human and veterinary subjects.

Production and Use of $\beta_2$m Fusion Proteins

Standard molecular biology, biochemistry and immunology methods are used in the present invention unless otherwise described. Such standard methods are described in Sambrook et al. (*Molecular Cloning: A Laboratory Manual*, Cold Spring Harbor, N.Y., 1989), Ausubel et al. (*Current Protocols in Molecular Biology*, Greene Publishing Associates and Wiley-lntersciences, 1987), Innis et al. (*PCR Protocols, A Guide to Methods and Applications*, Innis et al. (eds.), Academic Press, Inc., San Diego, Calif., 1990) and Harlow and Lane (*Antibodies, A Laboratory Manual*, Cold Spring Harbor Laboratory, New York, 1988). Methods of producing nucleic acid sequences expressing fusion proteins, as well as methods of expressing and purifying fusion proteins are well known in the art, and are described, for example, in U.S. Pat. Nos. 5,580,756 and 5,698,679. The following paragraphs are provided by way of guidance.

Standard techniques may be employed to make genetic constructs expressing $\beta_2$m fusion proteins, including restriction endonuclease digestion, ligation and the polymerase chain reaction. Any mammalian gene or cDNA encoding $\beta_2$m may be used as the source of the $\beta_2$m coding sequence. Such sequences are known in the art and are available on public databases such as GenBank. By way of example, the sequence of the human $\beta_2$m cDNA is described in Guessow et al. (*J. Immunol.* 139:3132–8, 1987, GenBank accession number: M17986). Notably, this cDNA sequence includes regions coding for the signal peptide of $h\beta_2$m (see FIG. 1).

Similarly, nucleic acid sequences coding for proteins that may be selected as the second domain of the fusion protein are well known in the art. While the selection of the second domain protein will typically be a co-stimulatory protein or a protein having some other immunological activity, fusion proteins may be constructed using $\beta_2$m as the second domain, and any protein that is desired to be delivered to the surface of a cell as the first domain. Examples of cDNAs encoding proteins having co-stimulatory activity include those encoding human B7.1 (Freeman et al., 1989, *J. Immu-* nol. 143:2714–22, GenBank accession number: M27533), B7.2 (Azuma et al., 1993. *Nature* 366:76–9, GenBank accession number L25259), LFA-3 (Wallner et al., 1987, *J. Exp. Med* 166:923–32, GenBank accession number Y00636) and ICAM-1 (Simmons et al., 1988, *Nature* 331:624–7, GenBank accession number X06990). Examples of other immunologically active proteins include, ICAM-3 (Fawcett et al., 1992, *Nature* 360:481–4, GenBank accession number S50015), VCAM-1 (Damle et al., 1992, *J. Immunol.* 148:1985–92), CD59 (Menu et al., 1994, *J. Immunol.* 153:2444–56), CD40 (Hancock et al., 1996, *Proc. Natl. Acad Sci. USA* 93:13967–72) and GM-CSF (Takashi et al., JP 1991155798-A, GenBank accession number E02975). Proteins having other activities, such as tumor necrosis factor (TNF, Masaaki et al., JP 1985185799, GenBank accession number E00423) may also be employed as the first domain in the fusion protein. By way of example, proteins that induce apoptosis (such as TNF) or anergy may be employed to delete certain classes of antigen-specific activated T-cells. Thus, myelin basic protein (MBP)-specific autoreactive T-cells that are found at the site of inflammation in multiple sclerosis patients may be deleted by introducing into the patient target cells that express MBP and which also present a TNF-$\beta_2$m fusion protein.

cDNA clones encoding $\beta_2$m and the second protein may be obtained as described in the cited references, or by PCR amplification from mRNA (or cDNA libraries) of cells that express the particular protein. cDNA amplification is performed as described by Innis et al. (*PCR Protocols, A Guide to Methods and Applications,* Innis et al. (eds.), Academic Press, Inc., San Diego, Calif., 1990) using primers designed to amplify the desired portions of the cDNA. For example, cDNA primers may be designed to amplify only that portion of the $\beta_2$m cDNA that encodes the mature form of $\beta_2$m. PCR may also be used to adapt the amplified fragments for ligation.

In addition to a $\beta_2$m domain and a second protein domain (e.g., B7), $\beta_2$m fusion proteins may also include additional elements, such as a linker sequence between the $\beta_2$m domain and the second domain, and a signal peptide. The linker sequence is generally between 10 and 25 amino acids in length, and serves to provide rotational freedom in the fusion construct, thereby facilitating appropriate conformational folding of the two adjacent protein domains. Such linker sequences are well known in the art and include the glycine (4)-serine spacer (GGGGS x3, Seq. ID. No. 11) described by Chaudhary et al. (*Nature* 339:394–397, 1989). A version of this linker in which the third repeat of the linker motif is modified to GGGAS (Seq. I.D. No. 12) is also shown in FIG. 3 and Seq. I.D. No. 2. Other linker sequences may also be used to construct the $\beta_2$m fusion proteins.

Signal peptides serve to direct expression of a particular protein to a specified location in the cell. Depending on whether the fusion protein is to be expressed in a prokaryotic or eukaryotic cell, a prokaryotic or eukaryotic signal peptide will be selected. Prokaryotic signal peptides that direct secretion of peptides into the medium may be particularly useful where large amounts of the fusion peptide are to be produced. Examples of such signal sequences include the prokaryotic signal sequence of the pectate lyase gene pelB (Power et al., 1992, *Gene* 113:95–9 (KYLLPTAAAGLLLLAAQPAMA, Seq. I.D. No. 13)), and the outer membrane protein ompT (Ouzzine et al., 1994, *FEBS Lett* 339:195–9 (MRAKLLGIVLTPIAISFAST, Seq. I.D. No. 14)). Eukaryotic signal peptides that direct expression of a peptide to the cell surface are useful where the fusion protein is to be presented on the surface of the cell. The signal peptide of $\beta_2$m (shown in FIG. 3 and Seq. I.D. No. 2) is particularly suitable for this purpose.

In their most basic form, nucleic acids encoding $\beta_2$m fusion proteins will comprise x-y wherein x is a nucleic acid sequence encoding the first protein domain (e.g., B7) and y is a nucleic acid sequence encoding the $\beta_2$m protein domain. Where a linker sequence is to be included, the nucleic acid may be represented as x-l-y, wherein l is a nucleic acid sequence encoding the linker peptide. Where a signal sequence is to be included, the nucleic acid may be represented as s-x-l-y wherein s is a nucleic acid sequence encoding the signal peptide. Preferably, although not necessarily, the relative orientation of the nucleic acid sequences is such that in the encoded fusion protein, the N-terminal of the $\beta_2$m protein is linked to the C-terminal of the second protein domain. In all instances, the various nucleic acid sequences that comprise the $\beta_2$m fusion protein construct (e.g., s, l, x and y) are operably linked such that the elements are situated in a single reading frame.

Nucleic acid constructs expressing fusion proteins may also include regulatory elements such as promoters, enhancers and 3' regulatory regions, the selection of which will be determined based upon the type of cell in which the protein is to be expressed. The constructs are the introduced into a vector suitable for expressing the $\beta_2$m fusion protein in the selected cell type.

A selected $\beta_2$m fusion protein may be obtained by expression in a prokaryotic or eukaryotic expression system, many of which are well known in the art. Heterologous proteins can be produced in prokaryotic cells by placing a strong, regulated promoter and an efficient ribosome binding site upstream of the $\beta_2$m fusion protein construct. Suitable promoter sequences include the beta-lactamase, tryptophan (trp), and lambda derived $P_L$ promoters. Prokaryotic expression vectors and expression systems suitable for producing high levels of protein bacterial cells are available commercially and include the pBAD, $P_L$ and Superlinker expression systems produced by Invitrogen (Carlsbad, Calif.) and the pMAL expression system produced by New England Biolabs (Beverly, Mass.). In addition, methods and plasmid vectors for producing heterologous proteins in bacteria are described in Sambrook et al. (*Molecular Cloning: A Laboratory Manual,* Cold Spring Harbor, N.Y., 1989). Often, proteins expressed at high levels are found in insoluble inclusion bodies; methods for extracting proteins from these aggregates are described by Sambrook et al. (*Molecular Cloning: A Laboratory Manual,* Cold Spring Harbor, N.Y., 1989, ch. 17). Vectors suitable for the production of intact native proteins include pKC30 (Shimatake and Rosenberg, 1981, *Nature* 292:128), pKK1177-3 (Amann and Brosius, 1985, *Gene* 40:183) and pET-3 (Studiar and Moffatt, 1986, *J. Mol. Biol.* 189:113). Suitable prokaryotic cells for expression of large amounts of $\beta_2$m fusion proteins include *Escherichia coli* and *Bacillus subtilis.*

Eukaryotic cells such as Chinese Hamster ovary (CHO), monkey kidney (COS), HeLa, *Spodoptera frugiperda,* and *Saccharomyces cerevisiae* may also be used to express $\beta_2$m fusion proteins. Regulatory regions suitable for use in these cells include, for mammalian cells, viral promoters such as those from CMV, adenovirus and SV40, and for yeast cells, the promoter for 3-phosphoglycerate kinase and alcohol dehydrogenase. Eukaryotic cell expression systems are also commercially available, and include *Pichia pastoris, Drosophila,* Baculovirus and Sindbis expression systems produced by Invitrogen (Carlsbad, Calif.).

The transfer of DNA into eukaryotic, in particular human or other mammalian cells, is now a conventional technique.

The vectors are introduced into the recipient cells as pure DNA (transfection) by, for example, precipitation with calcium phosphate (Graham and vander Eb, 1973, *Virology* 52:466) or strontium phosphate (Brash et al., 1987, *Mol. Cell Biol.* 7:2013), electroporation (Neumann et al., 1982, *EMBO J* 1:841), lipofection (Feigner et al., 1987, *Proc. Natl. Acad. Sci USA* 84:7413), DEAE dextran (McCuthan et al., 1968, *J. Natl Cancer Inst.* 41:351), microinjection (Mueller et al., 1978, *Cell* 15:579), protoplast fusion (Schafner, 1980, *Proc. Natl. Acad. Sci. USA* 77:2163–7), or pellet guns (Klein et al., 1987, *Nature* 327:70). Alternatively, the nucleic acid molecules can be introduced by infection with virus vectors. Systems are developed that use, for example, retroviruses (Bernstein et al., 1985, *Gen. Engr'g* 7:235), adenoviruses (Ahmnad et al., 1986, *J. Virol.* 57:267), or Herpes virus (Spaete et al., 1982, *Cell* 30:295).

The $\beta_2$m fusion protein produced in mammalian cells may be extracted following release of the protein into the supernatant and may be purified using an immunoaffinity column prepared using anti-$\beta_2$m antibodies. Alternatively, the $\beta_2$m fusion protein may be expressed as a chimeric protein with, for example, $\beta$-globin. Antibody to $\beta$-globin is thereafter used to purify the chimeric protein. Corresponding protease cleavage sites engineered between the $\beta$-globin gene and the nucleic acid sequence encoding the $\beta_2$m fusion protein are then used to separate the two polypeptide fragments from one another after translation. One useful expression vector for generating $\beta$-globin chimeric proteins is pSG5 (Stratagene).

By way of example cDNA encoding a $\beta_2$m fusion protein with an N-terminal methionine to initate translation may be subcloned into pET21-d (Novagen) which directs recombinant protein to inclusion bodies. Alternatively, commercially available insect cell expression systems such as the Baculovirus Expression Vector System from Pharmingen (San Diego, Calif.) can be used for the combined expression and folding of $\beta_2$m and $\beta_2$m fusion proteins, where the expressed proteins will require only subsequent purification.

Proteins expressed as described above may be further purified by immunoaffinity column and used directly to treat mammalian cells. Alternatively, expression of a $\beta_2$m fusion protein in a mammalian cell may be obtained by introducing a vector carrying a nucleic acid sequence encoding the protein into the cell. Nucleic acid molecules encoding $\beta_2$m fusion proteins carrying a signal sequence, such as the $\beta_2$m signal sequence are particularly preferred for this purpose.

In one aspect of the invention, the $\beta_2$m fusion proteins are used as immunotherapeutics, and the mammalian cell is a tumor cell. In many cancer patients, tumor cells escape immune recognition by downregulating MHC and/or co-stimulatory molecule expression. Accordingly, one method of treatment previously proposed is to remove tumor cells from a patient, introduce into the cells a co-stimulatory molecule such as B7 and then return the cells to the patient (see for example European Patent Application publication number EP 0 733 373 A2). Applying the discovery disclosed herein to those methods, introducing a $\beta_2$m fusion protein into tumor cells is expected to provide considerable benefit.

Obtaining $\beta_2$m fusion protein expression on the surface of tumor cells may be achieved either by directly incubating tumor cells with a purified preparation of the fusion protein, or by introducing into the cells a vector that expresses the fusion protein. All types of tumor are potentially amenable to treatment by this approach including, for example, carcinoma of the breast, lung, pancreas, ovary, kidney, colon and bladder, as well as melanomas and sarcomas.

Incorporation of the $\beta_2$m fusion protein onto the surface of tumor cells by incubation of the purified fusion protein with the cells, may be achieved by incubation of the tumor cells with the recombinant protein (1–5 $\mu$M) in serum-free medium for 2–16 hours. Additionally, tumor cells can be treated briefly with a low pH buffer (pH 2.5 to 3.5) to strip endogenous $\beta_2$m and peptide from cell-surface MHC I molecules followed by reconstitution with the $\beta_2$m fusion protein and relevant MHC I binding peptides for 1–16 hours.

Where a nucleic acid encoding the fusion protein is to be introduced into the tumor cell, the nucleic acid is preferably incorporated into a suitable expression vector. Suitable vectors include plasmid, cosmid and viral vectors, such as retroviruses, adenoviruses and herpesviruses. Disabled viruses, such as those described in U.S. Pat. No. 5,665,362 may be employed for this purpose. Because of the high efficiency with which viral vectors infect mammalian cells, viral vectors are expected to offer advantages over other vector types. The vector is then introduced into the tumor cell by one of a range of techniques, such as electroporation, lipofection, co-cultivation with virus-producing cells, or other standard means. In a preferred embodiment, the tumor cells are cells removed from the patient to be treated, but the tumor cells may alternatively be cells from a tumor cell line, such as the human tumor cell lines available from the American Type Culture Collection (ATCC, Manassas, Va.). If it is desired to screen the cells to select those into which the vector was introduced, this may be achieved by a number of means, including selecting for expression of the selectable marker if one is used, or screening for expression of the $\beta_2$m fusion protein on the surface of the cells. This latter procedure may be conveniently performed using a fluorescence activated cell sorter (FACS).

The tumor cells are subsequently administered to the patient in combination with a suitable carrier such as buffered water, saline, or glycine. In a preferred embodiment, where the tumor cells are cells originally removed from the patient, they are attenuated before being administered to the patient. An attenuated cell is one which is metabolically active but which is no longer able to proliferate. Methods for attenuating tumor cells are well known and include those described in EP 0 733 373 A2.

In an alternative embodiment, cell membranes from the tumor cells, which include the $\beta_2$m fusion protein, may be administered to the patient instead of intact tumor cells. A cell membrane preparation can readily be prepared by disrupting or lysing the cells using standard techniques, such as a French Press, freeze-thawing, or sonication. Following disruption of the cells, a membrane enriched fraction may be obtained by centrifugation.

The present invention also encompasses other immunotherapy methods for treating conditions such as cancer, including adoptive immunotherapy. As is known in the art, adoptive immunotherapy involves obtaining lymphoid cells exposed to a particular antigen, culturing those cells ex vivo under conditions whereby the activity of the cells is enhanced, and then administering the cells to an individual. The lymphoid cells are preferably T-cells removed from a cancer patient, for example T-cells from a draining lymph node. These T-cells are incubated with tumor cells removed from the patient which have been treated as described above so as to present a $\beta_2$m fusion protein on their cell surface. Accordingly, one aspect of the present invention is a form of adoptive immunotherapy in which the incubation of lymphoid cells ex vivo is performed in a medium containing tumor cells presenting a $\beta_2$m fusion protein prior to administration of the cells to a patient. The technical details of methods for obtaining lymphoid cells, ex vivo cultivation of such cells with immune stimulants, and administration to patients are known in the field and are described, for example in U.S. Pat. No. 4,690,915 ("Adoptive immunotherapy as a treatment modality in humans"), U.S. Pat. No. 5,229,115 ("Adoptive immunotherapy with interleukin-7"), 5,631,006 ("Immunotherapy protocol of culturing leukocytes in the presence of interleukin-2 in a hollow fiber cartridge"), and U.S. Pat. No. 4,902,288 ("Implantable immunotherapy system using stimulated cells"), and references cited therein.

Production and Use of h$\beta_2$m S55V and $\beta_2$m Fusion Proteins in Vaccine Preparations Methods for the production and use of $\beta_2$m as a vaccine adjuvant are known in the art and include those described in U.S. Pat. No. 5,733,550, which is incorporated herein by reference. Such methods may be applied for the use of h$\beta_2$m S55V as well as $\beta_2$m fusion proteins in vaccine preparations as well as methods of vaccination.

$\beta_2$m fusion proteins may be produced as described above. Nucleic acid molecules encoding forms of h$\beta_2$m carrying the S55V amino acid substitution may be produced using standard mutagenesis techniques, such as site directed mutagenesis, or by PCR as described in Example 4 below. The encoded h$\beta_2$m S55V may be expressed in and purified from prokaryotic or eukaryotic expression systems, as described above for the $\beta_2$m fusion proteins.

$\beta_2$m fusion proteins and h$\beta_2$m S55V may be used as adjuvants in vaccine preparations, in which case they may be combined with an antigen in a vaccine preparation, or they may be administered to a patient either shortly before or after administration of a conventional vaccine preparation. Preferably, the $\beta_2$m fusion protein or h$\beta_2$m S55V is administered at the same location and contemporaneously with the antigen preparation. Where a h$\beta_2$m fusion protein is used as a vaccine adjuvant, the h$\beta_2$m component of the protein may be a S55V form of h$\beta_2$m. The protein to which the $\beta_2$m is fused will preferably be a co-stimulatory protein such as B7.

Typically, the antigen administered to a patient in conjunction with a $\beta_2$m preparation of the present invention (i.e., a preparation of a $\beta_2$m fusion molecule or a S55V h$\beta_2$m) will be a peptide antigen that can bind to class I MHC molecules of the patient. Peptide antigens that may be employed include tumor antigens, as well as antigens from pathogenic organisms, including viruses and bacteria. Examples of suitable antigens include HIV gp120, sub-units of influenza nucieoprotein or hemagglutinin, and tumor antigens as discussed by Boon et al., (*Ann. Rev. Immunol.* 12:337–65, 1994); Finn (*Curr. Opin. Immunol.* 5:701–8, 1993) and Sligluff et al. (*Curr. Opin. Immunol.* 6:733–40, 1994). Such antigens may be isolated or extracted from an original source (e.g., tumor cells), or may be produced by recombinant means, or may be chemically synthesized. Vaccination may be accomplished by administering a single peptide antigen or a cocktail of antigens derived from one or more antigen sources.

The $\beta_2$m that forms the basis of the $\beta_2$m fusion protein or $\beta_2$m SS5V used in the vaccine compositions and methods of the present invention may be any mammalian $\beta_2$m. It may be preferable to use a $\beta_2$m derived from the same species of mammal as the mammal to be vaccinated so as to reduce the risk of immune response to the administered $\beta_2$m preparation. However, since xenogeneic $\beta_2$m is typically not inflammatory in vivo, this may not be necessary.

Vaccine preparations according to the present invention may be administered by any known means, including intramuscular and intravenous injection. In its simplest form, the $\beta_2$m preparation administered to the mammal is administered in conventional dosage form, preferably combined with a pharmaceutical excipient, carrier or diluent. Suitable pharmaceutical carriers may be solids or liquids, and may include buffers, anti-oxidants such as ascorbic acid, other polypeptides or proteins such as serum albumin, carbohydrates, chelating agents and other stabilizers and excipients. Suitable solid carriers include lactose, magnesium stearate, terra alba, sucrose, talc, stearic acid, gelatin, agar, pectin, acacia and cocoa butter. The amount of a solid carrier will vary widely depending on which carrier is selected, but preferably will be from about 25 mg to about 1 g per dose of active agent. Suitable liquid carriers include neutral buffered saline, optionally with suitable preservatives, stabilizers and excipients. The carrier or diluent may also include time delay material well known to the art such as, for example, glycerol distearate, either alone or with a wax. The foregoing examples of suitable pharmaceutical carriers are only exemplary and one of skill in the art will recognize that a very wide range of such carriers may be employed. Liposome-based delivery systems may also be employed to deliver $\beta_2$m preparations. Liposome-based systems, which may be employed to provide a measured release of the agent over time into the bloodstream, are well known in the art and are exemplified by the systems described in U.S. Pat. No. 4,356,167 ("Liposome drug delivery systems"), U.S. Pat. No. 5,580,575 ("Therapeutic drug delivery systems"), U.S. Pat. No. 5,595,756 ("Liposomal compositions for enhanced retention of bioactive agents") and 5,188,837 ("Liposphères for controlled delivery of substances"), and documents cited therein.

The formulation of the $\beta_2$m preparation with a pharmaceutical carrier can take many physical forms, but is preferably a sterile liquid suspension or solution, suitable for direct injection. Preferably, the patient will be administered the $\beta_2$m preparation in a formulation as described above (i.e. in combination with a pharmaceutical carrier), wherein the formulation includes a clinically effective amount of the agent. In the context of vaccination, "a clinically effective amount" of the $\beta_2$m preparation is an amount sufficient to provide an enhancement of the immune response to the target antigen, i.e., to produce a cytotoxic T-cell response greater than would be presented absent administration of the $\beta_2$m preparation. Quantification of the immune response arising from a vaccination may be achieved in any standard way, e.g., lymphoproliferation in response to test antigen in vitro or lysis of target cells by specific cytotoxic T-lymphocytes.

It will be appreciated that a clinically effective dose of a $\beta_2$m preparation will vary depending upon the actual $\beta_2$m being used (e.g., whether it is a $\beta_2$m fusion protein or $\beta_2$m S55V alone), and the characteristics of the patient (age, weight, other medications being taken etc.). Thus, the assessment of a clinically effective dosage will ultimately be decided by a physician, veterinarian, or other health care worker familiar with the patient. Typically, administering a $\beta_2$m preparation to a mammal as a component of a vaccination regimen will involve administration of from about 10 ng to 1 g of $\beta_2$m preparation per dose, with single dose units of from about 10 mg to 100 mg being commonly used, and specific dosages of up to 1 mg or 10 mg also being within the commonly used range. The amount of antigen included in the vaccine preparation that employs a $\beta_2$m adjuvant will typically be the same as would be included in vaccine preparations without the $\beta_2$m adjuvant, although greater or lesser amounts of antigen may be employed as clinically appropriate.

Where the $\beta_2$m is administered to the mammal in a single preparation with the vaccine antigens, the preparation may be formulated simply by mixing a clinically effective amount of the $\beta_2$m with the antigen preparation. Vaccines comprising tumor antigens and a $\beta_2$m may be prepared from tumor cells which have been transformed to express the $\beta_2$m.

EXAMPLES

The following examples serve to illustrate the invention.

EXAMPLE 1

Production of $\beta_2$m-B7 Fusion Protein

The murine B7.2:human $\beta_2$m fusion protein (mB7$\beta_2$) was made in multiple steps as follows. The extracellular domain of murine B7.2 (Freeman et al., 1993, *J. Exp. Med.* 178:2185–92, GenBank accession number L25606) was amplified by PCR from the plasmid mB7-2 (from Richard Hodes, NIH) using the following two oligonucleotides: mB7-2 5' PCR Oligo: AGGGTACCATGGTTTCCGTG-GAGACGCAAGC (Seq. I.D. No. 8) and mB7-2 3' PCR Oligo: TCGAATTCATGATGCTAGC-CCAATACGTTTGAGGAGATGG (Seq. I.D. No. 9) which have embedded restriction sites for cloning (bold): KpnI: GAATTC; NcoI: CCATGG; and BspHI: TGATCA.

The resulting PCR fragment was cut with NcoI and BspHI, and ligated as an amino terminal extension into an NcoI cut bluescript SK vector containing the signal peptide of h$\beta_2$m (Guessow et al., 1987, *J. Immunol.* 139:3132–8, GenBank accession number: M17986), the c-myc tag EQK-LISEEDLN (Zhou et al., 1996, *Mol Immunol.* 33:1127–34, Seq. I.D. No. 15), and full length h$\beta_2$m (plasmid #267). The resulting construct (plasmid #392) was then cut with NheI to linearize it 5' of the myc sequence. Synthetic oligonucleotides encoding a [gly4ser]$_3$ spacer were engineered with NheI compatible ends and ligated into the linearized vector to create plasmid #396. Finally, the entire coding sequence of wild-type h$\beta_2$m (without a myc tag) was PCR amplified from a h$\beta_2$m cDNA, with the addition of NheI site 5' and a Not I site 3' of the coding sequence. This product was digested with NheI and NotI, and subcloned into plasmid #396 that had also been digested with NheI and NotI to generate plasmid #406. This plasmid contained the signal sequence of h$\beta_2$m, followed by the extracellular domain of mB7.2, a 15 amino acid spacer, then mature h$\beta_2$m. For expression in bacteria, the eukaryotic signal sequence was removed. Thus, plasmid #406 was digested with NcoI and NotI to liberate the fusion protein without the signal peptide present, and this was then subcloned into the bacterial expression vector pE21-d that had been linearized with NcoI and NotI.

Following transfection of the BL21 (DE3) strain of *E. coli*, protein synthesis is induced with IPTG, cells were havested, lysed, and inclusion bodies washed and solubilized. Following refolding of the recombinant material, it was further purified by gel filtration and/or affinity chromatography with anti-$\beta_2$m antibodies. Experiments in which acid-stripped cells expressing only HLA-A2 were incubated under various conditions with the B7-$\beta_2$m fusion protein produced as described above, and then subjected to FACS analysis using conformationally-sensitive antibodies of varying specificities confirmed the following: (1) that the B7 domain of the fusion protein is natively folded; (2) that the $\beta_2$m domain of the fusion protein is natively folded; and (3) that the $\beta_2$m domain of the fusion protein functions to stabilize MHC I expression (data not shown).

EXAMPLE 2

The B7-$\beta_2$m Fusion Protein Co-stimulates T-Cells

The ability of B7-$\beta_2$m to co-stimulate splenic T-cells was determined in vitro. Antibodies specific for the B7 receptor CD28 were used as a control. $\beta_2$m, recombinant B7-$\beta_2$m, or anti-CD28 was added to the wells of a microtiter plate and incubated at 37° C. for 2 hours to promote binding. Thereafter the plates were washed to remove excess reagent, and splenic T-cells from BALB/c mice were added to the wells in the presence of sub-optimal concentrations of the soluble anti-T-cell receptor 2C11. The plates were incubated for 48 hours and then $^3$H-thymidine was added and allowed to incorporate into the proliferating cells for 20 hours. At the end of the time period, the cells were removed and the amount of $^3$H-thymidine taken up was measured.

Figure 5:
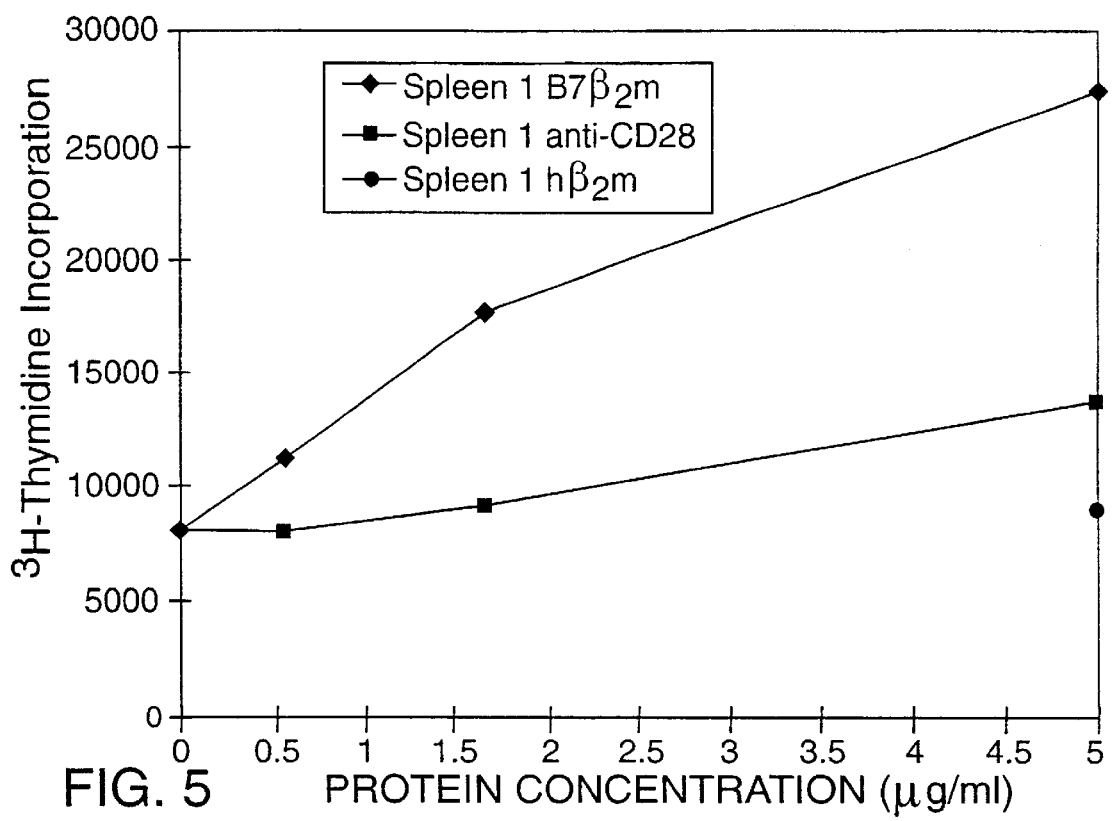
FIG. 5 is a graph showing the effect of plate-bound B7-β$_2$m on BALB/c splenic T-cell proliferation in the presence of a suboptimal concentration of soluble 2C11.

The results of these experiments showed that while no T-cell proliferation was observed in wells containing $\beta_2$m alone, recombinant B7-$\beta_2$m provides co-stimulation to the T-cells at least as effectively as the anti-CD28 antibody. A typical result is shown in FIG. 5.

EXAMPLE 3

Treatment of Tumor Cells with the $\beta_2$m-B7 Fusion Protein Boosts the Generation of Tumor-specific Cytotoxic T-cells The ability of the B7-$\beta_2$m fusion protein to stimulate T-cell recognition and response against tumor cell antigens was compared to the corresponding activity of h$\beta_2$m alone. DBA/2 mice were each vaccinated with 3×10$^6$ syngeneic P815 tumor cells that had been previously incubated in serum-free Iscove's Modified Dulbecco's Medium (SF IMDM) with either 0.2 $\mu$M B7-$\beta_2$m, 0.2 $\mu$M h$\beta_2$m alone, or no additional reagent. Samples of each type were analyzed by flow cytometry to show that they stained for B7 or h$\beta_2$m. These tumor cells were then irradiated with 20,000 Rads and injected into the mice. One week later the mice were reimmunized with identically prepared cells. After an additional week, the mice were sacrificed and their spleen cells were restimulated in culture with irradiated P815 stimulator cells for one week. The resulting cultured T-cells were then assayed for ability to kill untreated P815 tumor cells.

Figure 6:
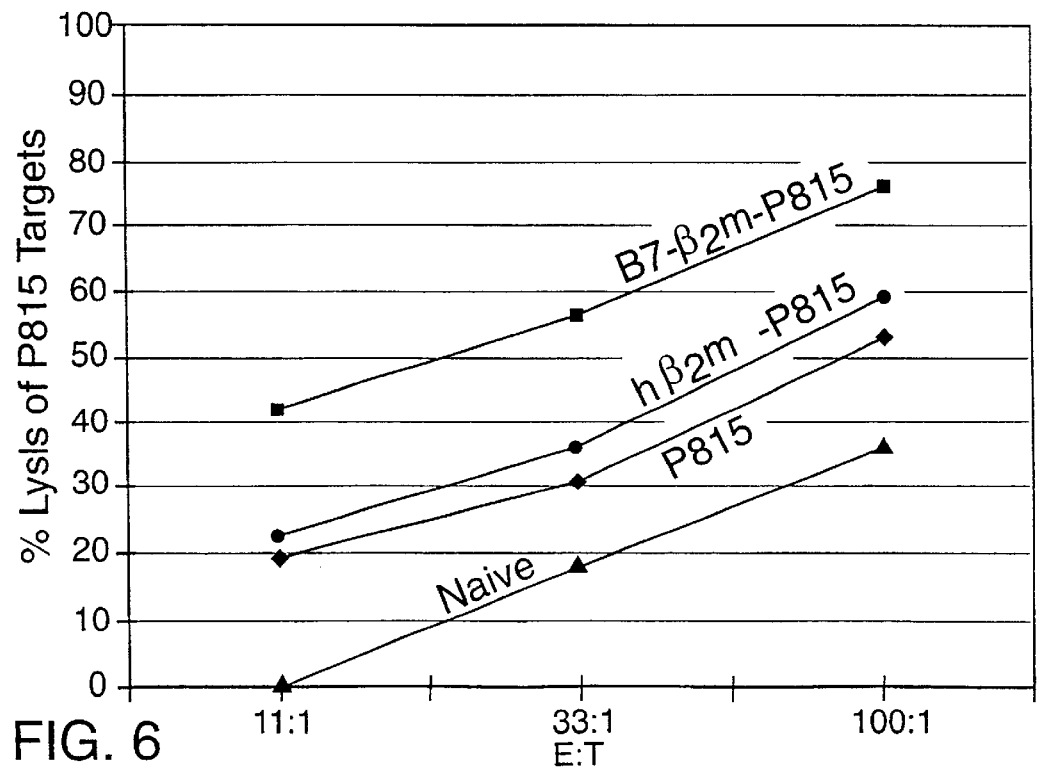
FIG. 6 is a graph showing the efficacy of P815 antigen-primed T-cells (primed with P815 cells presenting only P815 antigens, or P815 antigens and either B7-β$_2$m or β$_2$m) to lyse P815 tumor cells.

The results, depicted in FIG. 6, show that the spleen cells from the mice immunized with the B7-$\beta_2$m fusion protein-treated tumor cells were three fold more effective at killing tumor cells than cells from mice immunized with either the h$\beta_2$m treated or untreated tumor cells. These data show that the presence of the fusion protein on the tumor cell surface enhances the immune system response to the tumor antigens present on the tumor cell surface.

EXAMPLE 4

Production of High Affinity Variant of h$\beta_2$m

A number of variant forms of h$\beta_2$m were created and tested for activity using MHC stabilization, T-lymphocyte lysis and myc-h$\beta_2$m binding and inhibition assays. The hydrophilic serine 55 (S55) residue of h$\beta_2$m that is buried at the h$\beta_2$m/heavy chain interface and is situated directly adjacent to an ordered water molecule was identified as the target residue for mutagenesis. This residue was mutagenized to hydrophobic residues of increasing mass (valine, isoleucine, phenylalanine) in order to promote hydrophobic interactions and exclude the ordered water.

The h$\beta_2$m sequence variants were constructed by mutating h$\beta_2$m cDNA in Bluescript SK (Stratagene, La Jolla, Calif.) using the ExSite mutagenesis system (Stratagene) according to the manufacturer's protocol. The mutated cDNAs were subcloned into the bacterial expression vector pET-21d(+) (Novagen, Madison, Wis.) using engineered NcoI and BamHI sites at the 5' and 3' end of the mature protein sequence, respectively. Oligonucleotides used to create variants of the h$\beta_2$m sequence were as follows:

Sense S55F: 5' TTC TTC AGC AAG GAC TGG TCT TTC 3' (Seq. I.D. No. 4)

Sense S55I: 5' ATT TTC AGC AAG GAC TGG TCT TTC 3' (Seq. I.D. No. 5)

Sense S55V: 5' GTG TTC AGC AAG GAC TGG TCT TTC 3' (Seq. I.D. No. 6)

Common antisense: 5' TAA GTC TGA ATG CTC CAC TTT TTC 3' (Seq. I.D. No. 7)

Expression and purification of the mutated h$\beta_2$ms was performed as previously described by Shields et al. (*J. Immunol.* 160:2297–307, 1998). Briefly, h$\beta_2$m constructs in pET-21d(+) were transformed into the BL21(DE3) strain of *E. coli*. At an O.D. $_{600\ nm}$ of 0.6, cultures were induced with 1 mM IPTG for four hours, and inclusion bodies isolated by centrifugation after sonication of bacteria in 200 mM Tris, 2 mM EDTA, 10% Triton X-100, pH 7.6 and washing in 200 mM Tris, 2 mM EDTA, pH 7.6. Inclusion bodies were solubilized in 6 M Guanidine-HCl containing 0.3 M DTT, 100 mM Tris, pH 8.0, and a mixture of protease inhibitors (5 µg/ml Leupeptin, 0.5 mM AEBSF, 1% Aprotinin). Following overnight dialysis in 6 M Guanidine pH 2.0, recombinant protein was refolded over 72 h in 0.4 M Arginine, 5 mM oxidized glutathione, 100 mM Tris, 2 mM EDTA at 10° C. Following refolding, preparations were dialyzed exhaustively against 0.4 M Arginine, 100 mM Tris, 2 mM EDTA, pH 8.0 and then PBS at 4° C. Preparations were purified as a single peak by preparative FPLC on a Superdex 75 pg gel filtration column (Pharmacia, Uppsala, Sweden), concentrated using Centriprep-3 concentrating units (Amicon, Beverly, Mass.), sterile filtered and concentrations calculated based on O.D.$_{280\ nm}$ readings. Recombinant h$\beta_2$m was judged to be ≧95% pure based on analysis by SDS-PAGE, and analytical FPLC.

EXAMPLE 5 h$\beta_2$m S55V Produces Enhanced MHC I Stabilization

An HLA stabilization assay was used to screen the h$\beta_2$m variants. A number of HLA alleles, HLA-A1, HLA-A2, and HLA-A3, were analyzed in order to determine whether any of the point mutants exhibited allele-specific effects.

In this and the following experiments, cell lines, monoclonal antibodies (mAbs) and peptides used were as follows:
Cell Lines and Antibodies Hmy2.C1R cells (Storkus et al., 1987, *J. Immunol.* 138:1657) were stably transfected with HLA-A1, -A2, and -A3 as previously described (Winter et al., 1991,*J. Immunol.* 146:3508; DiBrino et al., 1993, *J. Immunol.* 151:5930). HLA-A2/HTLV-1 TAX 11–19 peptide-specific CTL clone N1218 and HLA-A3/Influenza NP 265–273 peptide clone 2G12 were isolated and restimulated as previously described by Biddison et al. (*J. Immunol.* 159:2018, 1997). All mAbs were used as culture supernatants grown in DMEM supplemented with 10% fetal calf serum, 20 mM HEPES, 2 mM L-glutamine, 1% non-essential amino acids, 1% Pen-strep, and 0.04 mg/ml of Gentamicin sulfate (complete DMEM). GAP.A3 (HLA-A3 specific), and BB7.5 (pan-HLA-ABC specific) hybridomas were obtained from the American Type Culture Collection (Manassas, Va.). The myc-specific 9E10 hybridoma has been previously described by Evan et al. (*Mol Cell Biol.* 5:3610–6, 1985). Unless otherwise noted all solutions used for cell growth were obtained from Biofluids (Rockville, Md.).
Peptides The peptides used were the HLA-A1 binding ornithine decarboxylase 309–317 (OD 309): SSEQTFMYY (Seq. I.D. No. 16); the HLA-A2 binding HTLV-1 TAX 11–19: LLFGYPVYV (SEQ. I.D. No. 17) and HIV gag 77–85: SLYNTVATL (Seq. I.D. No. 18); and the HLA-A3 binding pn2a.A3: KLYEKVYTYK (Seq. I.D. No. 19) and influenza NP 265–273: ILRGSVAHK (Seq. I.D. No. 20) (DiBrino et al., 1993, *Proc. Natl. Acad. Sci USA* 90:1508; DiBrino et al., 1994, *J. Immunol.* 152:620; Honma et al., 1997, *J. Neuroimmunol.* 73:7; Parker et al., 1992,*J. Immunol.* 149:3580; Parker et al., 1994, *J. Immunol.* 152:163; and Parker et al., 1995,*Immunol. Res.* 14:34). These peptides were purchased from Bachem (Torrance, Calif.) or provided by Dr. John E. Coligan (Natl. Inst. of Allergy and Infectious Diseases, NIH). All peptides were purified by reverse phase HPLC and were >95% pure as determined by analytical HPLC and mass spectrometry.

The MHC stabilization was done essentially as described previously (Bremers et al., 1995, *J. Immunol. Emphasis Tumor Immunol.* 18:77; van der Burg et al., 1995, *Hum. Immunol.* 44:189; Sugawara et al., 1987, *J. Immunol. Methods* 100:83) with minor modifications. Briefly, Hmy2.C1R cells (Storkus et al., 1987, *J. Immunol.* 138:1657) were stably transfected with HLA-A1, -A2, and -A3 as previously described (Winter et al., 1991; *J. Immunol.* 146:3508; DiBrino et al., 1993, *J. Immunol.* 151:5930). Hmy2.C1R-A1, -A2, and -A3 cells were washed twice with PBS, resuspended in 0.13 M citric acid, 66 mM Na$_2$HPO$_4$, pH 2.9 (pH 3.2 for A2 cells), for 90 seconds at 4° C., washed with two 50 ml changes of IMDM, and resuspended in SF IMDM (identical to SF DMEM using IMDM instead). 10$^5$ cells per well were added to a 96 well microtiter plate containing hybridoma supernatants, peptide, and h$\beta_2$m dilutions in a total volume of 150 µl. HLA-A1 transfected Hmy2.C1R cells were combined with BB7.5 mAb and 10 µg/ml A1-binding OD 309 peptide. HLA-A2 transfected Hmy2.C1R cells were combined with BB7.5 mAb and 2.5 µg/ml A2-binding HIV gag peptide. HLA-A3 transfected Hmy2.C1R cells were combined with GAP.A3 mAb and 1.25 µg/ml A3-binding pn2a.A3 peptide. After a four hour incubation at 23° C., cells were washed twice with FACS buffer (PBS, 2 mg/ml BSA, 0.02% NaN$_3$) and stained with FITC-conjugated goat anti-mouse IgG (H+L) F(ab')$_2$ fragment (Cappel/Organon Teknika, Durham, N.C.) for one hour at 4° C. Cells were washed twice with FACS buffer and fixed in 1% formaldehyde in PBS followed by flow cytometric analysis on a FACScan II machine (Becton Dickinson, Mountain View, Calif.).

Figure 7A:
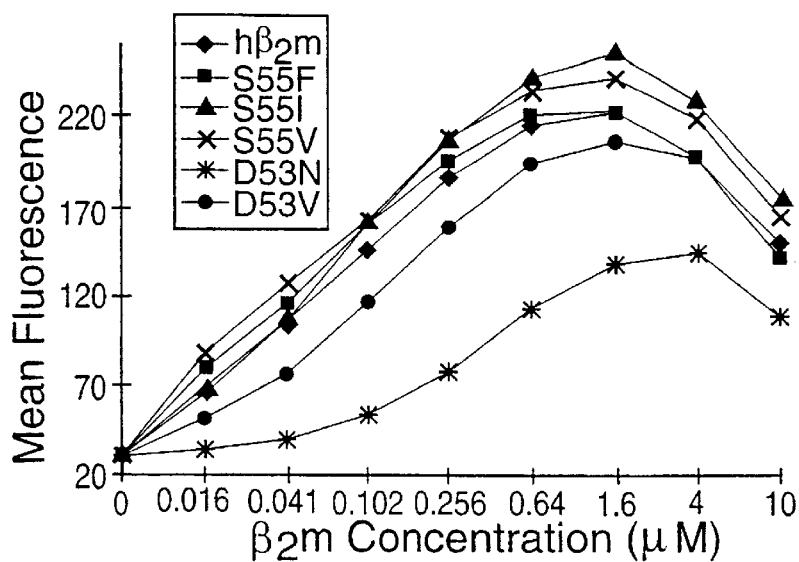
FIGS. 7a–7c are graphs illustrating the stabilization of cell-surface HLA-A1 (a), -A2 (b), and -A3 (c) by mutant hβ$_2$m and peptide. All values are expressed as mean fluorescence intensity.
Figure 7B:
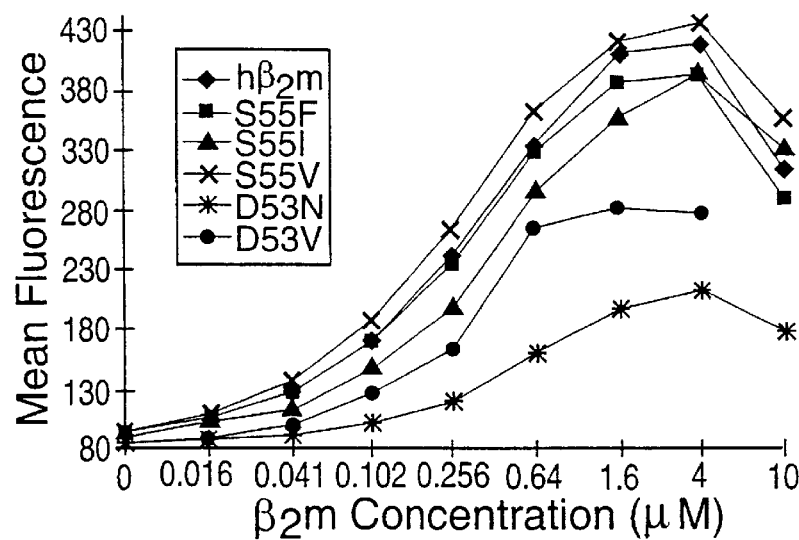
Figure 7C:
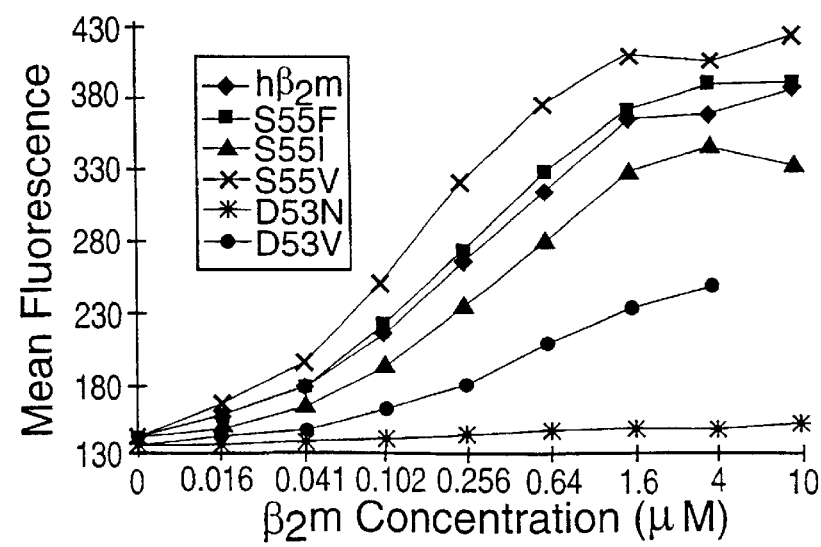

FIG. 7 demonstrates the ability of the S55 variant h$\beta_2$m to stabilize HLA-A1 (FIG. 7*a*), HLA-A2 (FIG. 7*b*), and HLA-A3 (FIG. 7*c*) in the presence of a specific binding peptide and an appropriate HLA-specific antibody. The S55V variant ("X" symbol in FIG. 7) stabilized HLA-A1 and HLA-A3 approximately 2-fold and 3-fold better respectively, than wild-type h$\beta_m$m (diamonds) at a molar level, and effects on HLA-A2 stabilization by S55V were slightly better than those observed with wild-type h$\beta_2$m. S55F (squares) was similar to wild-type h$\beta_2$m for all alleles tested, while the effects of S55I (triangles) varied depending on the allele (better with HLA-A1 and worse with -A2 and -A3).

EXAMPLE 6 hβ₂m S55V Binds to MHCI with a Higher Affinity that Wild-type hβ₂m

The antibodies used in the experiments in the previous Example were selected due to their dependence on both hβ₂m and peptide in order to detect "complete" molecules, i.e. heavy chain/hβ₂m/peptide natively folded trimeric complexes. Since this binding assay requires the presence of an antibody in addition to hβ₂m and peptide (van der Burg, 1995, *Hum. Immunol.* 44:189), there was the possibility that the antibody itself exerted an effect that is specific for a particular hβ₂m mutant. Due to concerns regarding the potential contribution of the antibodies to the stabilization of cell-surface MHC I complexes, a binding inhibition assay was developed that directly measures the relative abilities of hβ₂ms to bind to MHC I molecules. This assay format requires a labeled hβ₂m to measure the inhibition. Methods of labeling such as biotinylation and iodination are random reactions and create multiply labeled species needing further purification prior to use in a proper competition assay (Hochman et al., 1988, *J. Immunol.* 140:2322). However, endogenous labeling with an epitope tag creates an uniquely labeled species of hβ₂m. Additionally, tyrosine and lysine residues (common targets of biotinylation and iodination) known to be at the MHC heavy chain/hβ₂m interface would not be affected with an endogenous label. Therefore an epitope tag (myc) was engineered onto the amino terminus of hβ₂m and the ability of the various hβ₂m mutants to compete with the myc-hβ₂m for cell-surface binding using the anti-myc mAb 9E10 was studied.

To establish the functional activity of the myc-hβ₂m itself, direct binding studies were performed. Briefly, Hmy2.C1R transfectant cells at $2.5 \times 10^5$ per tube in a 500 µl volume were incubated at 37° C. for 16 hours in SF IMDM with 2.5 µM myc-β₂m, 20 µg/ml peptide and the indicated concentrations of inhibitor β₂m. The OD 309 peptide was used for HLA-A1, the HIV gag peptide for HLA-A2, and the pn2a.A3 peptide for HLA-A3. Cells were washed three times in plain IMDM followed by incubation with 9E10 (anti-myc) hybridoma supernatant at 4° C. for one hour. After washing with IMDM, cells were stained for one hour with FITC anti-mouse IgG at 4° C. Cells were washed a final time in FACS buffer and analyzed by flow cytometry, gating on live (propidium iodide-excluding) cells. In the presence of an appropriate peptide there was concentration-dependent myc-β₂m binding for all alleles studied. However, when cells were incubated with myc-β₂m in the absence of peptide, no appreciable myc-hβ₂m binding was observed.

Figure 8A:
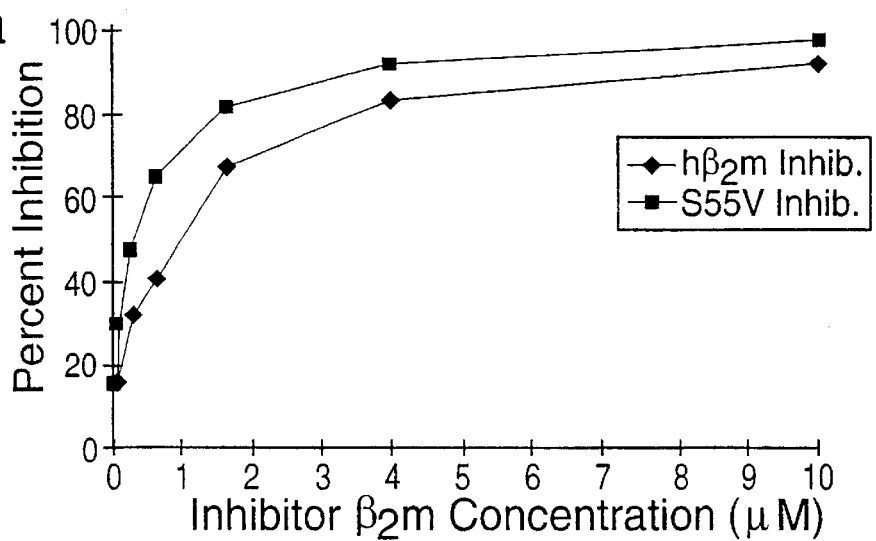
FIGS. 8a–8c are graphs showing the inhibition of myc-β$_2$m binding by S55V and hβ$_2$m to cell-surface HLA-A1 (a), -A2 (b), and -A3 (c). All values are expressed as mean fluorescence intensity.
Figure 8B:
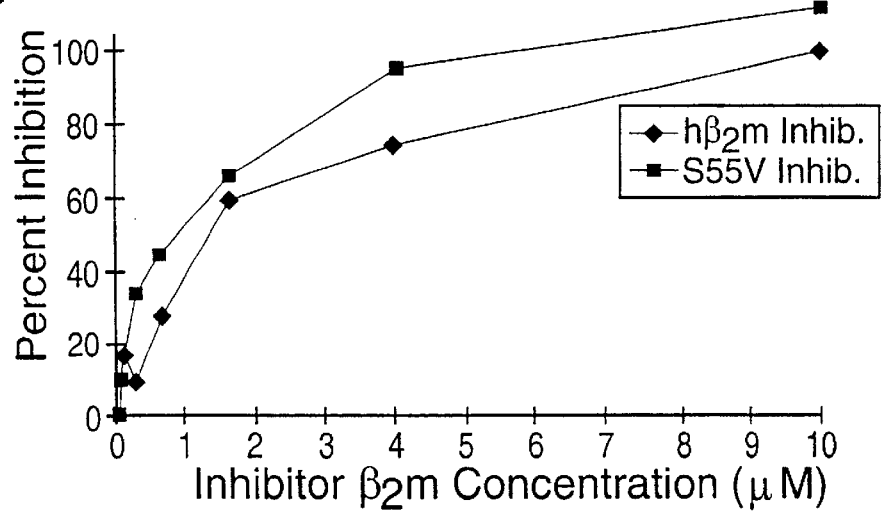
Figure 8C:
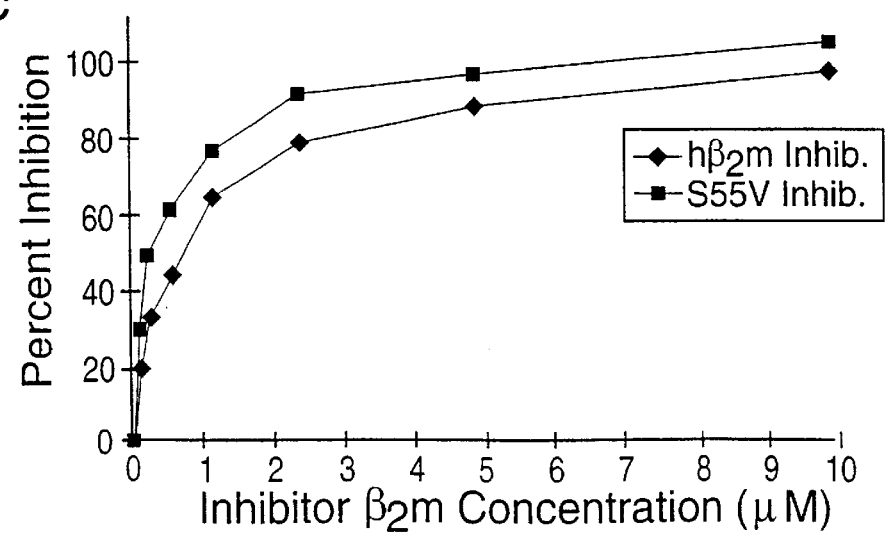

The relative abilities of wild-type hβ₂m and S55V to inhibit the binding of myc-hβ₂m to HLA molecules were next compared using an inhibition assay. The inhibition assay was identical to the binding assay with the following modifications: 2.5 µM myc-hβ₂m was used in all cases and different concentrations of non-myc labeled recombinant hβ₂m were included to inhibit myc-hβ₂m binding to cell surface MHC molecules. Percent inhibition was calculated by the following equation: (1-((experimental-background)/(no inhibitor-background)))×100. 10–20,000 gated events per sample were counted, and all experiments were repeated at least twice. Compared with wild-type hβ₂m, the S55V mutant inhibited myc-hβ₂m binding about 2.5-fold better at a molar level for HLA-A1, -A2, and -A3 (FIG. 8). These results demonstrate the higher relative affinity of the S55V mutant compared to wild-type hβ₂m for HLA-A1 (FIG. 8*a*), -A2 (FIG. 8*b*) and -A3 (FIG. 8*c*).

EXAMPLE 7 hβ₂m S55V Enhances CTL Recognition of Target Cells

Figure 9A:
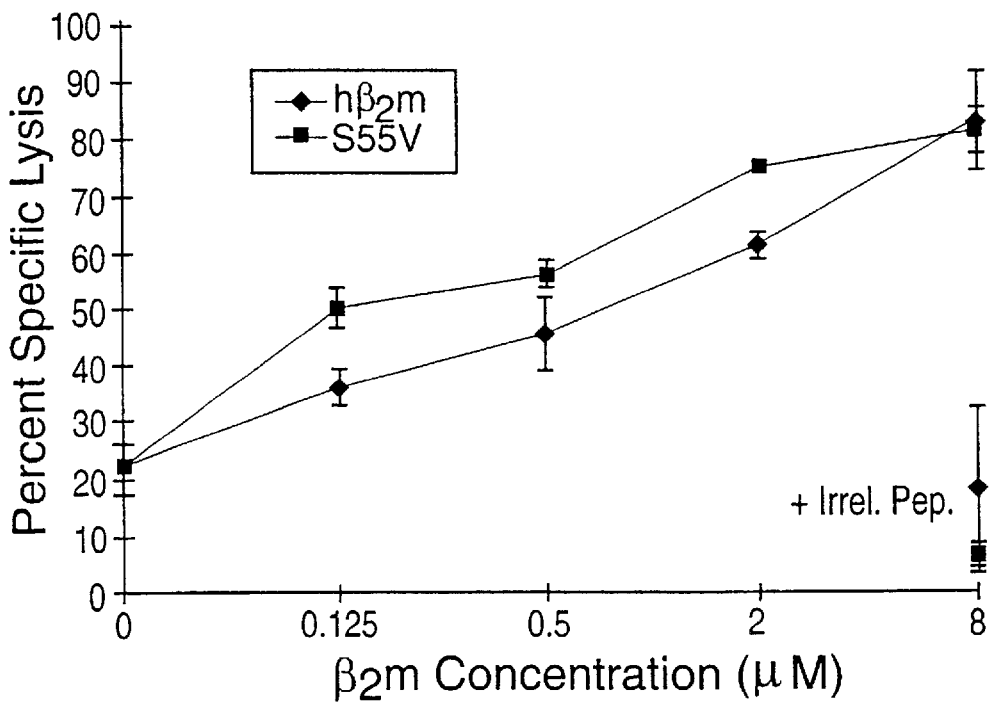
FIGS. 9a–9b are graphs illustrating that the S55V mutant enhances CTL recognition better than wild-type hβ$_2$m in both Hmy2.C1R-A2 (a) and Hmy2.C1R-A3 (b) target cells.

The effectiveness of hβ₂m in facilitating exogenous peptide loading of MHC I molecules was measured using a CTL lysis assay (Depierreux et al., 1997, *J. Immunol. Methods* 203:77) as follows: Hmy2.C1R cells transfected with HLA-A2 or HLA-A3 were resuspended to $4 \times 10^6$ cells/ml in complete DMEM supplemented with 20 µM BATD (which forms a fluorescent chelate with Europium; Wallac, Gaithersburg, Md.) and incubated at 37° C. for 30–60 minutes. Cells were resuspended in 10 ml of serum free (SF) CTL medium (IMDM supplemented with 5 mg/ml bovine serum albumin (Sigma, St. Louis, Mo.), 2 mM L-glutamine, 1.25 mM sulfinpyrazone (Sigma), and 1% Pen-strep), centrifuged and washed once more with SF CTL medium. Cells were then pulsed with peptide and/or β₂m in SF CTL medium for 60–90 minutes at 37° C. Cells were washed twice in SF CTL medium, resuspended in CTL medium (5% fetal calf serum in lieu of BSA) and combined at the designated effector:target ratio with CTL clones in round bottom microtiter plates (CTL clone N1218 at an E:T ratio of 4:1 (FIG. 9*a*) or the NP-specific HLA-A3 restricted CTL clone 2711 at an E:T ratio of 2:1 (FIG. 9*b*)). Plates were gently centrifuged at 100×g for 2 minutes and then incubated at 37° C. for 2 hours. Finally, plates were centrifuged at 300×g and 20 µl per well was transferred to 200 µl of 0.3 M acetic acid, 60 mM sodium acetate, 7.5 µg/ml Europium (Aldrich, Milwaukee, Wis.), and the plate read on a Wallac 1234 DELFIA Fluorometer. Percent specific lysis was calculated with the following equation:

$$100 \times ((\text{experimental-blank}) - (\text{spontaneous-blank}))/((\text{maximum-blank}) - (\text{spontaneous-blank})).$$

In this assay, target cell lysis not only correlates with the loading of a specific peptide antigen, but it also demonstrates that the peptide is bound in an immunologically relevant manner. Hmy2.C1R-A2 target cells (a human lymphoblastoid cell essentially null for HLA molecules except for the transfected HLA-A2.1) (Winter et al., 1991; *J. Immunol.* 146:3508; DiBrino et al., 1993, *J. Immunol.* 151:5930) were pulsed with a suboptimal concentration of HTLV-1 TAX peptide ($9.3 \times 10^{-12}$ M/l) or control A2-binding HIV gag peptide at $1 \times 10^{-9}$ M/l for 90 minutes in serum-free CTL medium in the absence or presence of increasing concentrations of purified, recombinant hβ₂m and then used as targets in a conventional lysis assay. The presence of wild-type hβ₂m dramatically increased the specific lysis by the TAX-specific CTL clone in a dose-dependent fashion. Using this suboptimal concentration of peptide there was 20% lysis in the absence of hβ₂m. Addition of 8 µM hβ₂m increases the lysis to the maximal observed at this E:T ratio. In the absence of hβ₂m 100 fold higher concentration of peptide would be required to achieve comparable levels of lysis (data not shown).

Figure 9B:
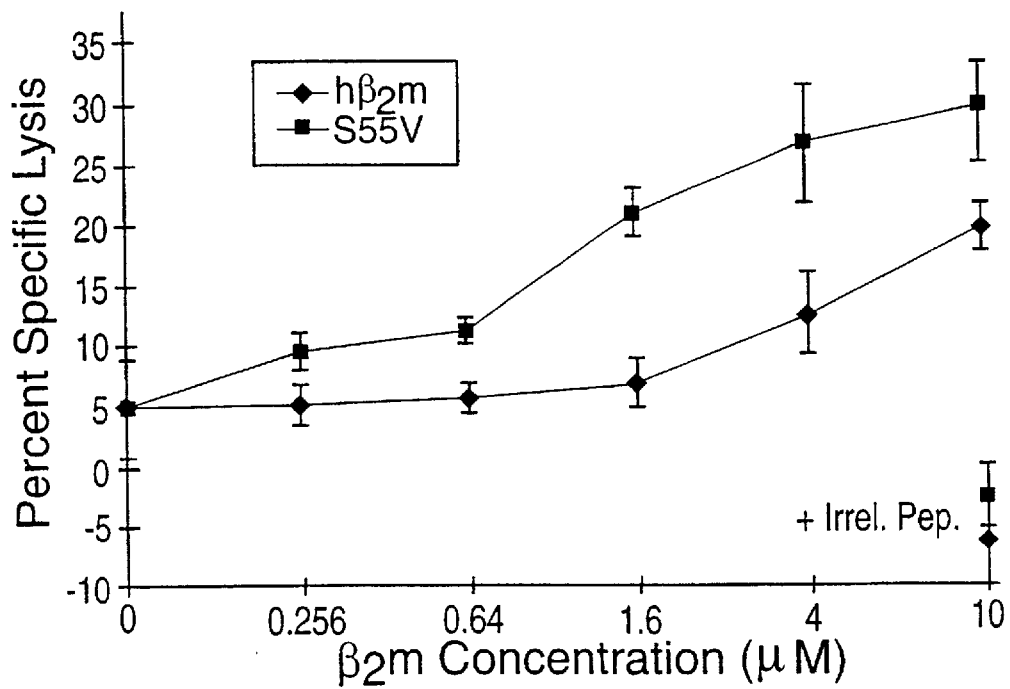

Having established the ability of wild-type hβ₂m to enhance the loading of antigenic peptide onto cells, the activity of the S55V variant in this assay was examined. Two CTL clones, specific for an HTLV-1 TAX peptide in the context of HLA-A2 and an influenza nucleoprotein peptide in the context of HLA-A3, were used in the assay described above using Hmy2.C1R transfectants pulsed with a suboptimal concentration of antigenic peptide (NP 265–273, $1 \times 10^{-10}$ M/l) or control A3-binding pn2a.A3 peptide at $1 \times 10^{-6}$ M/l. The S55V mutant was 4-fold more effective at a molar level than wild-type hβ₂m at enhancing target cell lysis for HLA-A2 (FIG. 9*a*) and 6 to 7-fold better for HLA-A3 (FIG. 9*b*). Controls with irrelevant -A2 and -A3 binding peptides with the highest concentrations of hβ₂m used resulted in only background levels of killing.

Additionally, multiple TAX-specific A2-restricted clones displayed similar levels of S55V enhanced killing relative to wild-type $\beta_2$m (data not shown).

In view of the many possible embodiments to which the principles of the invention may be applied, it will recognized that the foregoing examples are offered for purposes of illustration and do not limit the scope of the invention. Rather, the scope of the invention is defined by the following claims. We therefore claim as our invention all that comes within the scope and spirit of these claims.

We claim:

1. A fusion protein comprising a first amino acid sequence and a second amino acid sequence, wherein the second amino acid sequence is human $\beta_2$-microglobulin S55V ($h\beta_2m$ S55V) (SEQ ID NO: 10).

2. The fusion protein of claim 1, wherein the first amino acid sequence comprises B7.1, B7.2, a lymphocyte function-associated (LFA) protein, or an intercellular adhesion molecule (ICAM).

3. The fusion protein of claim 2, wherein the LFA protein comprises LFA-1 or LFA-3.

4. The fusion protein of claim 2, wherein the ICAM comprises ICAM-1 or ICAM-2.

5. A fusion protein comprising first and second domains, wherein the first domain is B7.1, B7.2, a lymphocyte function-associated (LFA) protein, or an intercellular adhesion molecule (ICAM) and the second domain is $\beta_2m$.

6. The fusion protein of claim 5, wherein the LFA protein comprises LFA-1 or LFA-3.

7. The fusion protein of claim 5, wherein the ICAM comprises ICAM-1 or ICAM-2.

8. The fusion protein of claim 5, wherein the first domain is joined to an amino terminus of the second domain.

9. The fusion protein of claim 5, wherein the second domain is $h\beta_2m$.

10. The fusion protein of claim 9, wherein the $h\beta_2m$ is $h\beta_2m$ S55V (SEQ ID NO: 10).

11. The fusion protein of claim 9, wherein the protein has an amino acid sequence as shown in SEQ ID NO: 2 or 3.

12. The fusion protein of claim 5, wherein the first and second domains are linked by a peptide linker.

13. The fusion protein of claim 5, wherein the fusion protein further comprises a signal peptide joined to an amino terminus of the first domain.

14. The fusion protein of claim 13, wherein the signal peptide is a $\beta_2m$ signal peptide.

15. A fusion protein comprising first and second domains, wherein the first domain comprises B7.1, B7.2, LFA-3, or ICAM-1, and the second domain comprises $\beta_2m$.

16. A fusion protein comprising a structure X-Y, wherein X is B7.1, B7.2, a lymphocyte function-associated (LFA) protein, or an intercellular adhesion molecule (ICAM), and Y is a $\beta_2m$.

17. The fusion protein of claim 16, wherein the LFA protein comprises LFA-1 or LFA-3.

18. The fusion protein of claim 16, wherein the ICAM comprises ICAM-1 or ICAM-2.

19. The fusion protein of claim 16, wherein the protein comprises a structure X-L-Y wherein L is a linker peptide.

20. The fusion protein of claim 19, wherein the protein comprises a structure S-X-L-Y wherein S is a signal peptide.

21. The fusion protein of claim 20, wherein the signal peptide is a $\beta_2$m signal peptide.

22. The fusion protein of claim 16 wherein the protein has an amino acid sequence as shown in SEQ ID NO: 2 or 3.

23. An isolated human $\beta_2$-microglobulin molecule having a valine residue present at position 55 in mature wild-type h$\beta_2$m instead of a serine residue.

24. The isolated human $\beta_2$-microglobulin molecule of claim 23, wherein the molecule comprises the amino acid sequence shown in SEQ ID NO: 10.

25. A recombinant nucleic acid molecule encoding the fusion protein of claim 1.

26. A recombinant nucleic acid molecule encoding the fusion protein of claim 5.

27. A recombinant nucleic acid molecule encoding the fusion protein of claim 16.

28. A recombinant nucleic acid molecule encoding the h$\beta_2$m molecule of claim 23.

29. A vector comprising the recombinant nucleic acid of claim 25.

30. A vector comprising the recombinant nucleic acid of claim 26.

31. A vector comprising the recombinant nucleic acid of claim 27.

32. A vector comprising the recombinant nucleic acid of claim 28.

33. A transgenic cell comprising the recombinant nucleic acid molecule of claim 25.

34. A transgenic cell comprising the recombinant nucleic acid molecule of claim 26.

35. A transgenic cell comprising the recombinant nucleic acid molecule of claim 27.

36. A transgenic cell comprising the recombinant nucleic acid molecule of claim 28.

37. A cell having a cell membrane comprising the fusion protein of claim 1.

38. The cell of claim 37, wherein the cell is a tumor cell.

39. A cell having a cell membrane comprising the fusion protein of claim 5.

40. The cell of claim 39, wherein the cell is a tumor cell.

41. A cell having a cell membrane comprising the fusion protein of claim 16.

42. The cell of claim 41, wherein the cell is a tumor cell.

43. A cell having a cell membrane comprising the h$\beta_2$m molecule of claim 23.

44. The cell of claim 43, wherein the cell is a tumor cell.

45. A method of enhancing an immune response of a mammal to an antigen presented on a surface of a cell, comprising:

contacting the cell with the fusion protein of claim 1 such that the fusion protein is presented on the surface of the cell; and administering the cell to the mammal.

46. The method of claim 45, wherein the cell is a tumor cell.

47. A method of enhancing an immune response of a mammal to an antigen presented on a surface of a cell, comprising:

contacting the cell with the fusion protein of claim 5 such that the fusion protein is presented on the surface of the cell; and administering the cell to a mammal.

48. The method of claim 47, wherein the cell is a tumor cell.

49. A method of enhancing an immune response of a mammal to an antigen presented on a surface of a cell, comprising:

contacting the cell with the fusion protein of claim 16 such that the fusion protein is presented on the surface of the cell; and administering the cell to a mammal.

50. The method of claim 49, wherein the cell is a tumor cell.

51. A method of enhancing an immune response of a mammal to an antigen presented on a surface of a cell, comprising:

contacting the cell with the h$\beta_2$m molecule of claim 23 such that the h$\beta_2$m molecule is presented on the surface of the cell; and administering the cell to a mammal.

52. The method of claim 51, wherein the cell is a tumor cell.

53. A method of enhancing an immune response of a mammal to an antigen presented on a surface of a cell, comprising:

transforming the cell with the recombinant nucleic acid molecule of claim 25, such that expression of the nucleic acid molecule results in expression of a fusion protein encoded by the nucleic acid molecule being presented on the surface of the cell; and administering the cell to a mammal.

54. The method of claim 53, wherein the cell is a tumor cell.

55. A method of enhancing an immune response of a mammal to an antigen presented on a surface of a cell, comprising:

transforming the cell with the recombinant nucleic acid molecule of claim 26, such that expression of the nucleic acid molecule results in expression of a fusion protein encoded by the nucleic acid molecule being presented on the surface of the cell; and administering the cell to a mammal.

56. The method of claim 55, wherein the cell is a tumor cell.

57. A method of enhancing an immune response of a mammal to an antigen presented on a surface of a cell, comprising:

transforming the cell with the recombinant nucleic acid molecule of claim 27, such that expression of the nucleic acid molecule results in expression of a fusion protein encoded by the nucleic acid molecule being presented on the surface of the cell; and administering the cell to a mammal.

58. The method of claim 57, wherein the cell is a tumor cell.

59. A method of enhancing an immune response of a mammal to an antigen presented on a surface of a cell, comprising:

transforming the cell with the recombinant nucleic acid molecule of claim 28, such that expression of the nucleic acid molecule results in expression of a protein encoded by the nucleic acid molecule being presented on the surface of the cell; and administering the cell to a mammal.

60. The method of claim 59, wherein the cell is a tumor cell.

61. A method of stimulating a tumor-reactive cytotoxic T-cell response, comprising:

isolating T-cells from a patient having a tumor;

isolating tumor cells from the patient;

incubating the tumor cells with the fusion protein of claim 1, such that the fusion protein is presented on the surface of the tumor cells;

incubating the T-cells in the presence of the fusion protein-presenting tumor cells to increase the number of tumor-reactive T-cells; and administering a therapeutically effective dose of the tumor-reactive T-cells to the patient.

62. A method of stimulating a tumor-reactive cytotoxic T-cell response, comprising:

isolating T-cells from a patient having a tumor;

isolating tumor cells from the patient;

incubating the tumor cells with the fusion protein of claim 5, such that the fusion protein is presented on the surface of the tumor cells;

incubating the T-cells in the presence of the fusion protein-presenting tumor cells to increase the number of tumor-reactive T-cells; and administering a therapeutically effective dose of the tumor-reactive T-cells to the patient.

63. A method of stimulating a tumor-reactive cytotoxic T-cell response, comprising:

isolating T-cells from a patient having a tumor;

isolating tumor cells from the patient;

incubating the tumor cells with the fusion protein of claim 16, such that the fusion protein is presented on the surface of the tumor cells;

incubating the T-cells in the presence of the protein-presenting tumor cells to increase the number of tumor-reactive T-cells; and administering a therapeutically effective dose of the tumor-reactive T-cells to the patient.

64. A method of stimulating a tumor-reactive cytotoxic T-cell response, comprising:

isolating T-cells from a patient having a tumor;

isolating tumor cells from the patient;

incubating the tumor cells with the $h\beta_2m$ molecule of claim 23, such that the $h\beta_2m$ molecule is presented on the surface of the tumor cells;

incubating the T-cells in the presence of the protein-presenting tumor cells to increase the number of tumor-reactive T-cells; and administering a therapeutically effective dose of the tumor-reactive T-cells to the patient.

* * * * *

UNITED STATES PATENT AND TRADEMARK OFFICE
CERTIFICATE OF CORRECTION

PATENT NO. : 6,682,741 B1
DATED : January 27, 2004
INVENTOR(S) : Ribaudo et al.

It is certified that error appears in the above-identified patent and that said Letters Patent is hereby corrected as shown below:

Title page,
Item [56], References Cited, OTHER PUBLICATIONS, "Fukazawa et al." reference, "β-Microglubulins" should be -- β-Microglobulins--, and the page numbers "3542-3550" should be -- 3543-3550 --.
"Gerstmayer et al." reference, "1584584-4590" should be -- 158:4584-4590 --.
"Uger et al." reference, "β-MicroglobulinConstructs," should be -- β-Microglobulin Constructs, --.

Column 4,
Line 49, "h$β_2$m." should be -- h$β_2$m. --.

Column 5,
Line 17, "protien" should be -- protein --.

Column 10,
Line 24, "are the introduced" should be -- are then introduced --.
Line 50, "pKK1177-3" should be -- pKK177-3 --.

Column 11,
Line 6, "Feigner et al." should be -- Felgner et al. --.
Line 31, "initate" should be -- initiate --.

Column 13,
Line 38, "h$β_2$m." should be -- h$β_2$m. --.
Line 48, "nucieoprotein" should be -- nucleoprotein --.
Line 59, "SS5V" should be -- S55V --.

Column 15,
Line 25, "GAATFC" should be -- GAATTC --.
Line 41, "Not I" should be -- NotI --.
Line 45, "h$β_2$m," should be -- h$β_2$m, --.
Line 55, "havested" should be -- harvested --.

UNITED STATES PATENT AND TRADEMARK OFFICE
CERTIFICATE OF CORRECTION

PATENT NO. : 6,682,741 B1
DATED : January 27, 2004
INVENTOR(S) : Ribaudo et al.

It is certified that error appears in the above-identified patent and that said Letters Patent is hereby corrected as shown below:

Column 19,
Line 2, "MHCI" should be -- MHC I --.
Line 3, "that" should be -- than --.
Line 21, "creates an uniquely" should be -- creates a uniquely --.
Line 59, "SS5V" should be -- S55V --.

Signed and Sealed this

Thirteenth Day of July, 2004

JON W. DUDAS
*Acting Director of the United States Patent and Trademark Office*

SEQUENCE LISTING

```
<160> NUMBER OF SEQ ID NOS: 20

<210> SEQ ID NO 1
<211> LENGTH: 119
<212> TYPE: PRT
<213> ORGANISM: Homo sapiens

<400> SEQUENCE: 1

Met Ser Arg Ser Val Ala Leu Ala Val Leu Ala Leu Leu Ser Leu Ser
 1               5                  10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 2
<211> LENGTH: 339
<212> TYPE: PRT
<213> ORGANISM: Artificial Sequence
<220> FEATURE:
<223> OTHER INFORMATION: Description of Artificial Sequence: fusion
      protein

<400> SEQUENCE: 2

Met Val Ser Val Glu Thr Gln Ala Tyr Phe Asn Gly Thr Ala Tyr Leu
 1               5                  10                  15

Pro Cys Pro Phe Thr Lys Ala Gln Asn Ile Ser Leu Ser Glu Leu Val
            20                  25                  30

Val Phe Trp Gln Asp Gln Gln Lys Leu Val Leu Tyr Glu His Tyr Leu
        35                  40                  45

Gly Thr Glu Lys Leu Asp Ser Val Asn Ala Lys Tyr Leu Gly Arg Thr
    50                  55                  60

Ser Phe Asp Arg Asn Asn Trp Thr Leu Arg Leu His Asn Val Gln Ile
65                  70                  75                  80

Lys Asp Met Gly Ser Tyr Asp Cys Phe Ile Gln Lys Lys Pro Pro Thr
                85                  90                  95

Gly Ser Ile Ile Leu Gln Gln Thr Leu Thr Glu Leu Ser Val Ile Ala
            100                 105                 110

Asn Phe Ser Glu Pro Glu Ile Lys Leu Ala Gln Asn Val Thr Gly Asn
        115                 120                 125

Ser Gly Ile Asn Leu Thr Cys Thr Ser Lys Gln Gly His Pro Lys Pro
```

```
                130             135             140
Lys Lys Met Tyr Phe Leu Ile Thr Asn Ser Thr Asn Glu Tyr Gly Asp
145                 150                 155                 160

Asn Met Gln Ile Ser Gln Asp Asn Val Thr Glu Leu Phe Ser Ile Ser
                165                 170                 175

Asn Ser Leu Ser Leu Ser Phe Pro Asp Gly Val Trp His Met Thr Val
            180                 185                 190

Val Cys Val Leu Glu Thr Glu Ser Met Lys Ile Ser Ser Lys Pro Leu
        195                 200                 205

Asn Phe Thr Gln Glu Phe Pro Ser Pro Gln Thr Tyr Trp Ala Ser Thr
    210                 215                 220

Ser Gly Gly Gly Gly Ser Gly Gly Gly Ser Gly Gly Gly Ala Ser
225                 230                 235                 240

Ile Gln Arg Thr Pro Lys Ile Gln Val Tyr Ser Arg His Pro Ala Glu
                245                 250                 255

Asn Gly Lys Ser Asn Phe Leu Asn Cys Tyr Val Ser Gly Phe His Pro
                260                 265                 270

Ser Asp Ile Glu Val Asp Leu Leu Lys Asn Gly Glu Arg Ile Glu Lys
            275                 280                 285

Val Glu His Ser Asp Leu Ser Phe Ser Lys Asp Trp Ser Phe Tyr Leu
        290                 295                 300

Leu Tyr Tyr Thr Glu Phe Thr Pro Thr Glu Lys Asp Glu Tyr Ala Cys
305                 310                 315                 320

Arg Val Asn His Val Thr Leu Ser Gln Pro Lys Ile Val Lys Trp Asp
                325                 330                 335

Arg Asp Met

<210> SEQ ID NO 3
<211> LENGTH: 358
<212> TYPE: PRT
<213> ORGANISM: Artificial Sequence
<220> FEATURE:
<223> OTHER INFORMATION: Description of Artificial Sequence: fusion
      protein

<400> SEQUENCE: 3

Met Ser Arg Ser Val Ala Leu Ala Val Leu Ala Leu Leu Ser Leu Ser
 1               5                  10                  15

Gly Leu Glu Ala Val Ser Val Glu Thr Gln Ala Tyr Phe Asn Gly Thr
                20                  25                  30

Ala Tyr Leu Pro Cys Pro Phe Thr Lys Ala Gln Asn Ile Ser Leu Ser
            35                  40                  45

Glu Leu Val Val Phe Trp Gln Asp Gln Gln Lys Leu Val Leu Tyr Glu
        50                  55                  60

His Tyr Leu Gly Thr Glu Lys Leu Asp Ser Val Asn Ala Lys Tyr Leu
65                  70                  75                  80

Gly Arg Thr Ser Phe Asp Arg Asn Asn Trp Thr Leu Arg Leu His Asn
                85                  90                  95

Val Gln Ile Lys Asp Met Gly Ser Tyr Asp Cys Phe Ile Gln Lys Lys
                100                 105                 110

Pro Pro Thr Gly Ser Ile Ile Leu Gln Gln Thr Leu Thr Glu Leu Ser
            115                 120                 125

Val Ile Ala Asn Phe Ser Glu Pro Glu Ile Lys Leu Ala Gln Asn Val
        130                 135                 140

Thr Gly Asn Ser Gly Ile Asn Leu Thr Cys Thr Ser Lys Gln Gly His
```

```
                        145                 150                 155                 160
Pro Lys Pro Lys Lys Met Tyr Phe Leu Ile Thr Asn Ser Thr Asn Glu
                165                 170                 175
Tyr Gly Asp Asn Met Gln Ile Ser Gln Asp Asn Val Thr Glu Leu Phe
            180                 185                 190
Ser Ile Ser Asn Ser Leu Ser Leu Ser Phe Pro Asp Gly Val Trp His
        195                 200                 205
Met Thr Val Val Cys Val Leu Glu Thr Glu Ser Met Lys Ile Ser Ser
    210                 215                 220
Lys Pro Leu Asn Phe Thr Gln Glu Phe Pro Ser Pro Gln Thr Tyr Trp
225                 230                 235                 240
Ala Ser Thr Ser Gly Gly Gly Ser Gly Gly Gly Ser Gly Gly
                245                 250                 255
Gly Ala Ser Ile Gln Arg Thr Pro Lys Ile Gln Val Tyr Ser Arg His
            260                 265                 270
Pro Ala Glu Asn Gly Lys Ser Asn Phe Leu Asn Cys Tyr Val Ser Gly
        275                 280                 285
Phe His Pro Ser Asp Ile Glu Val Asp Leu Leu Lys Asn Gly Glu Arg
    290                 295                 300
Ile Glu Lys Val Glu His Ser Asp Leu Ser Phe Ser Lys Asp Trp Ser
305                 310                 315                 320
Phe Tyr Leu Leu Tyr Tyr Thr Glu Phe Thr Pro Thr Glu Lys Asp Glu
                325                 330                 335
Tyr Ala Cys Arg Val Asn His Val Thr Leu Ser Gln Pro Lys Ile Val
            340                 345                 350
Lys Trp Asp Arg Asp Met
        355

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
ttcttcagca aggactggtc tttc                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
attttcagca aggactggtc tttc                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 6
gtgttcagca aggactggtc tttc                                              24

<210> SEQ ID NO 7
```

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
taagtctgaa tgctccactt tttc                                      24

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 8
agggtaccat ggtttccgtg gagacgcaag c                              31

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 9
tcgaattcat gatgctagcc caatacgttt gaggagatgg                     40

<210> SEQ ID NO 10
<211> LENGTH: 99
<212> TYPE: PRT
<213> ORGANISM: Artificial Sequence
<220> FEATURE:
<223> OTHER INFORMATION: Description of Artificial Sequence: Modified
      hB2m S55V

<400> SEQUENCE: 10

Ile Gln Arg Thr Pro Lys Ile Gln Val Tyr Ser Arg His Pro Ala Glu
  1               5                  10                  15

Asn Gly Lys Ser Asn Phe Leu Asn Cys Tyr Val Ser Gly Phe His Pro
                 20                  25                  30

Ser Asp Ile Glu Val Asp Leu Leu Lys Asn Gly Glu Arg Ile Glu Lys
             35                  40                  45

Val Glu His Ser Asp Leu Val Phe Ser Lys Asp Trp Ser Phe Tyr Leu
         50                  55                  60

Leu Tyr Tyr Thr Glu Phe Thr Pro Thr Glu Lys Asp Glu Tyr Ala Cys
 65                  70                  75                  80

Arg Val Asn His Val Thr Leu Ser Gln Pro Lys Ile Val Lys Trp Asp
                 85                  90                  95

Arg Asp Met

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: linker that
      can be used in fusion proteins

<400> SEQUENCE: 11

Gly Gly Gly Gly Ser Gly Gly Gly Ser Gly Gly Gly Gly Ser
  1               5                  10                  15
```

```
<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: linker that
      can be used in fusion proteins

<400> SEQUENCE: 12

Gly Gly Gly Gly Ser Gly Gly Gly Ser Gly Gly Gly Ala Ser
 1               5                  10                 15

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: signal
      peptide

<400> SEQUENCE: 13

Lys Tyr Leu Leu Pro Thr Ala Ala Ala Gly Leu Leu Leu Leu Ala Ala
 1               5                  10                  15

Gln Pro Ala Met Ala
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: signal
      peptide

<400> SEQUENCE: 14

Met Arg Ala Lys Leu Leu Gly Ile Val Leu Thr Pro Ile Ala Ile Ser
 1               5                  10                  15

Phe Ala Ser Thr
            20

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: c-myc tag

<400> SEQUENCE: 15

Glu Gln Lys Leu Ile Ser Glu Glu Asp Leu Asn
 1               5                  10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:  ornithine
      decarboxylase 309-317

<400> SEQUENCE: 16

Ser Ser Glu Gln Thr Phe Met Tyr Tyr
 1               5

<210> SEQ ID NO 17
<211> LENGTH: 9
<212> TYPE: PRT
```

```
<213> ORGANISM: Artificial Sequence
<220> FEATURE:
<223> OTHER INFORMATION: Description of Artificial Sequence: HTLV TAX
      11-19

<400> SEQUENCE: 17

Leu Leu Phe Gly Tyr Pro Val Tyr Val
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: HIV gag
      77-85

<400> SEQUENCE: 18

Ser Leu Tyr Asn Thr Val Ala Thr Leu
 1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: pn2a.A3

<400> SEQUENCE: 19

Lys Leu Tyr Glu Lys Val Tyr Thr Tyr Lys
 1               5                  10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: influenza
      NP 265-273

<400> SEQUENCE: 20

Ile Leu Arg Gly Ser Val Ala His Lys
 1               5
```